United States Patent
Young et al.

(10) Patent No.: US 8,563,304 B2
(45) Date of Patent: Oct. 22, 2013

(54) LOW OXYGEN CULTURE CONDITIONS FOR MAINTAINING RETINAL PROGENITOR CELL MULTIPOTENCY

(75) Inventors: Michael J. Young, Gloucester, MA (US); Budd A. Tucker, Coralville, IA (US); Petr Y. Baranov, Somerville, MA (US)

(73) Assignee: The Schepens Eye Research Institute, Boston, MA (US)

( * ) Notice: Subject to any disclaimer, the term of this patent is extended or adjusted under 35 U.S.C. 154(b) by 2 days.

(21) Appl. No.: 13/160,002

(22) Filed: Jun. 14, 2011

(65) Prior Publication Data

US 2012/0321593 A1   Dec. 20, 2012

(51) Int. Cl.
*C12N 5/071* (2010.01)
(52) U.S. Cl.
USPC .......................... 435/325; 435/366; 424/93.7
(58) Field of Classification Search
USPC .................................. 435/325, 366; 424/93.7
See application file for complete search history.

(56) References Cited

U.S. PATENT DOCUMENTS

| | | | |
|---|---|---|---|
| 4,683,195 | A | 7/1987 | Mullis et al. |
| 6,117,675 | A | 9/2000 | van der Kooy et al. |
| 6,610,540 | B1 | 8/2003 | Csete et al. |
| 6,638,369 | B1 | 10/2003 | Tucker et al. |
| 6,759,242 | B1 | 7/2004 | Csete et al. |
| 7,514,259 | B2 | 4/2009 | Young et al. |

OTHER PUBLICATIONS

Lange et al. (2011) Retina-specific activation of a sustained hypoxia-like response leads to severe retinal degeneration and loss of vision, Neurobiology of Disease, 41, 119-130; Available online Sep. 15, 2010.*
Rooprai et al. (2000) The effects of exogenous growth factors on matrix metalloproteinase secretion by human brain tumor cells, British Journal of Cancer 82(1), 52-55.*
Fischer et al. (2002) Exogenous Growth Factors Stimulate the Regeneration of Ganglion Cells in the Chicken Retina, Developmental Biology, 251, 367-379.*
Biology online, Definition of "Expression," Accessed onlilne on Aug. 29, 2012 at www.biology-online.org/dictionary/Expression.*
D'Ippolito et al., Low Oxygen tension inhibits osteogenic differentiation and enhances stemness of human MIAMI cells, Bone, 39 (2006) 513-522.*
Ezashi et al., (2005) Low O2 tensions and the prevention of differentiation of hES cells, PNAS, 2005, vol. 102, No. 13, 4783-4788.*
Sanghera et al., The PI3K/Akt/mTOR pathway mediates retinal progenitor cell survival under hypoxic and superoxide stress, Molecular and Cellular Neuroscience, 47: 145-153, available online Apr. 2, 2011.*
Santilli et al., Mild Hypoxia Enhances Proliferation and Multipotency of Human Neural Stem Cells, Jan. 2010, vol. 5, Issue 1.*
Tomita et al., Bone marrow-derived stem cells can differentiation into retinal cells in injured rat retina, Stem Cells, 2002, 20: 279-283.*
Van Patot et al., Hypoxia: adapting to high altitude by mutating EPAS-1 the gene encoding HIF-2 alpha, High Altitude Medicine and Biology 12.2 (Jun. 2011): 157(11).*
Klassen, H. J. et al., "Multipotent Retinal Progenitors Express Development Markers, Differentiate into Retinal Neurons, and Preserve Light-Mediated Behavior", Invest. Opthalmol. Vis. Sci., 2004, 45(11), pp. 4167-4173.
Klassen, H. et al., "Isolation of Retinal Progenitor Cells from Post-Mortem Human Tissue and Comparison with Autologous Brain Progenitors", J. Neuroscience Research, 2004, 77(3), pp. 334-343.
Klassen, H. et al., "Progenitor Cells from the Porcine Neural Retina Express Photoreceptor Markers after Transplantation to the Subretinal Space of Allorecipeints", Stem Cells, 2007, 25(5); pp. 1222-1230.

* cited by examiner

*Primary Examiner* — Karen Cochrane Carlson
*Assistant Examiner* — Jennifer M. H. Tichy
(74) *Attorney, Agent, or Firm* — Novak Druce Connolly Bove + Quigg LLP

(57) ABSTRACT

The present invention relates to methods for culturing human retinal progenitor cells under low oxygen conditions to allow the cells to retain the ability to differentiate into photoreceptors following transplantation. The described methods provide cells that can treat a number of ocular diseases, including retinitis pigmentosa and age-related macular degeneration.

9 Claims, 22 Drawing Sheets

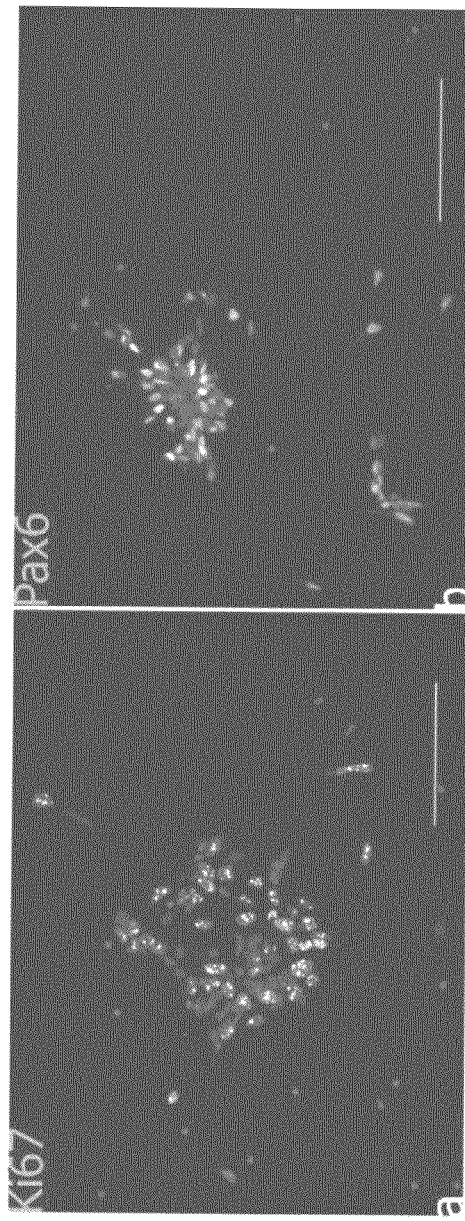
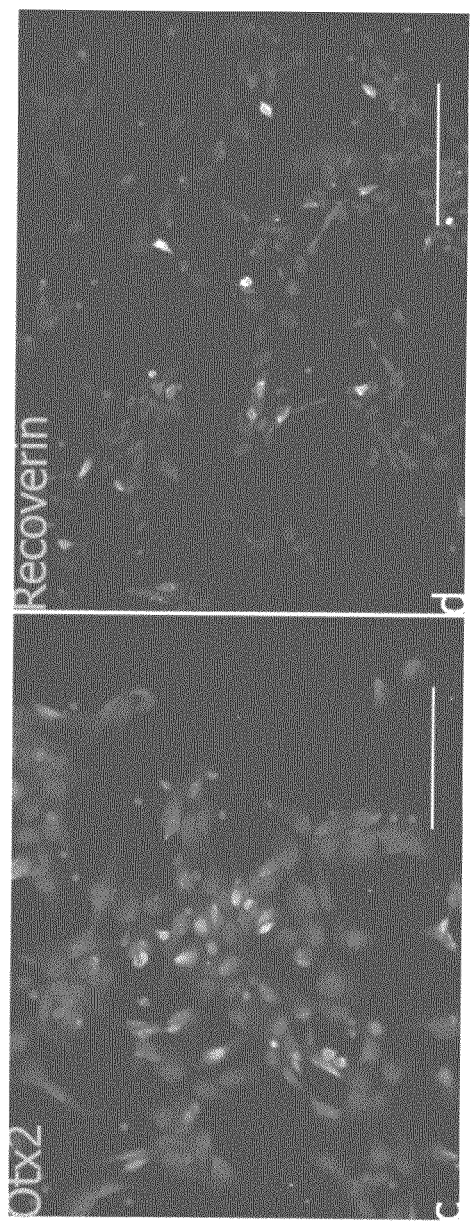
FIG. 2A  FIG. 2B  FIG. 2C  FIG. 2D

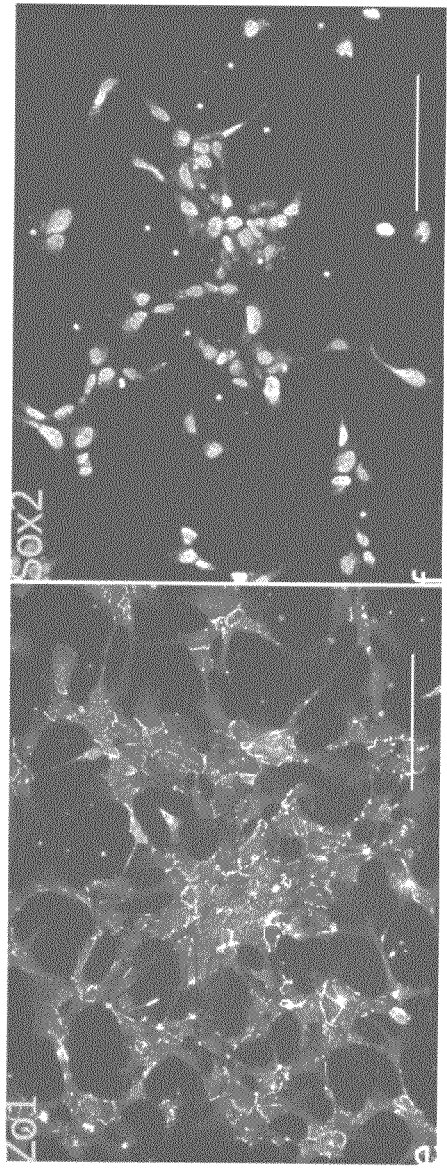
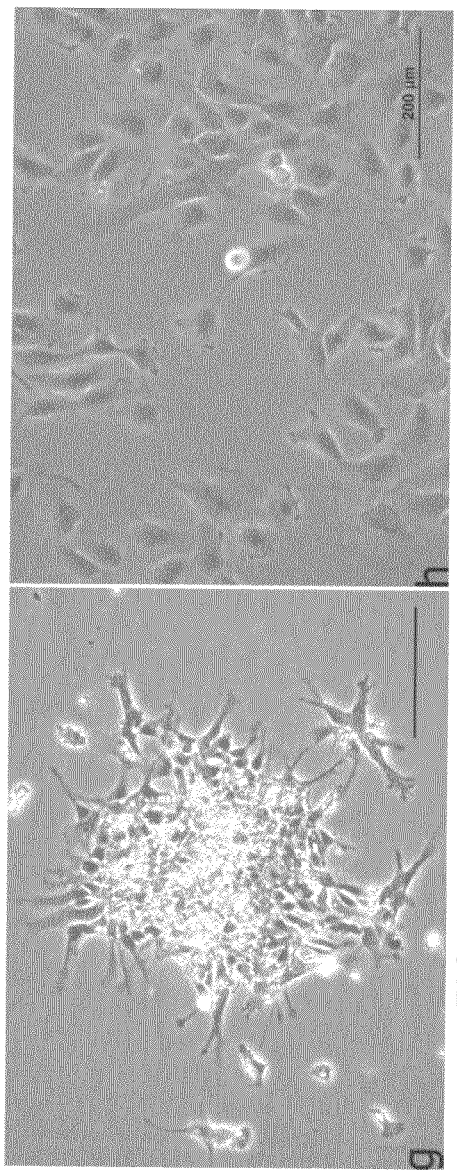
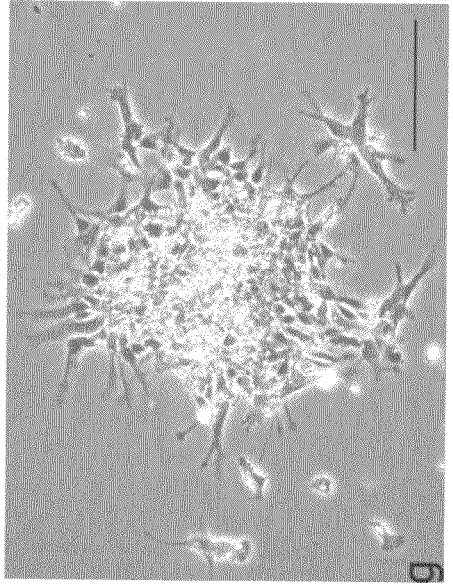
FIG. 2E  FIG. 2F  FIG. 2G  FIG. 2H

LOW OXYGEN CULTURE CONDITIONS FOR MAINTAINING RETINAL PROGENITOR CELL MULTIPOTENCY

BACKGROUND OF THE INVENTION

The human retina is part of the central nervous system and, both developmentally and phenotypically, the retina shares the recalcitrance of brain and spinal cord with respect to functional repair. This is unfortunate in that, among heritable conditions alone, there are many examples of diseases involving the loss of retinal neurons. For example, retinitis pigmentosa, age-related macular degeneration and diabetic retinopathy are diseases characterized by the progressive death of light sensing photoreceptor cells of the retina. These diseases are the leading causes of incurable blindness in the western world, and are increasing rapidly in the developing Eastern world.

Since the intrinsic regenerative capacity of the human retina is extremely limited, a promising potential therapy for these diseases currently in research is a focus on cellular replacement. One strategy for replacing these cells has been to transplant retinal tissue from healthy donors to the retina of the diseased host. While the results of such studies have been encouraging in terms of graft survival, the problem of integration between graft and host has proved daunting. Laboratory studies have focused on multipotent stem cells (also variously referred to as progenitor cells, immature cells, undifferentiated cells or proliferative cells) for transplantation and differentiation. Proliferative stem or progenitor cells have been isolated from the hippocampus in laboratory animals, cultured and transplanted into various sites within the central nervous system (CNS) to subsequently differentiate into neurons and glial cells. Similarly, adult hippocampal cells have been shown to be capable of migrating into, and differentiating within, the mature dystrophic retina.

The isolation of true stem cells from the neuroretina, particularly cells able to differentiate into functional photoreceptor cells both in vitro and in vivo, has proven elusive. Putative retinal stem cells derived from the ciliary marginal zone pigment epithelial layer are described in U.S. Pat. No. 6,117,675. While these cells are said to be capable of proliferating in the absence of growth factor, there is no evidence that these cells are capable of integrating into a host retina and differentiating into functional mature cells in vivo.

Commonly assigned U.S. Pat. No. 7,514,259 is directed to neuroretina-derived photoreceptor cells which are capable of repopulating a human retina. These cells are derived from neural retinal tissue by removing the ciliary marginal zone and the optic nerve to eliminate contamination, and can be obtained from post-natal tissue.

Apart from difficulties involving the identification of viable human retinal progenitor cells, there are significant limitations involving the ability to culture these cells. Although such cells posses the capacity to survive, to differentiate into retinal neurons, and to integrate within the dystrophic host retina following transplantation, these cells have limited proliferative capacity. This represents a clear distinction between human retinal progenitor cells and other less restricted undifferentiated cell types, such as embryonic stem cells or induced pluripotent stem cells, which may not share such limitations.

For instance, and following isolation, human retinal progenitor cells can only be passaged a maximum number of seven (7) times in vitro without loss of multipotency, including the ability to proliferate in vivo and to form mature retinal cell types. This greatly limits the number of cells that can be obtained from a single isolate, the number of transplants that can be performed from a single cell isolation, and the further clinical application of these cells.

Attempts to immortalize fetal human retinal cells using SV40 transfection have not proven successful since the cells fail to express the markers of mature differentiated cells after transplantation. Similarly, other methods for culturing cells, such as the conditional immortalization or downregulation of pRb, as described for Muller glial cell lines expressing retinal stem cell genes, also yield cells which fail to differentiate into photoreceptors.

A variety of stem cell types have included, inter alia, the use of low oxygen culture conditions. See, for instance, U.S. Pat. No. 6,759,242 and U.S. Pat. No. 6,610,540 which relate to the enhanced differentiation of CNS precursor cells and neural crest stem cells under low oxygen culture conditions.

In view of the aforementioned, as well as the importance of human retinal progenitor cells for clinical evaluation and use, it will readily be appreciated that a need exists to improve the ability of such cells to reproduce in vitro while maintaining multipotency properties in vivo. These and other objectives of the invention will be clear from the following description.

SUMMARY OF THE INVENTION

The invention is directed to the use of low oxygen culture conditions for enhancing the expression of retinal progenitor cells in vitro, and for maintaining the multipotency of the cells in vivo following transplantation into a host. The progenitor cells according to the invention are capable of retinal-specific differentiation into photoreceptors, and are therefore useful for the treatment of retinal diseases upon transplantation into a diseased eye. Thus, the invention provides a method to obtain a population of multipotent retinal progenitor cells in vitro suitable for in vivo transplantation into a host recipient. In one aspect, the population of multipotent progenitor cells is substantially homogeneous, e.g. clonally expanded.

According to the invention, human retinal progenitor cells are obtained from viable neuroretinal source tissue, such as the retinal neurosphere. The cells can be added to a suitable cell culture media containing nutrients, buffering agents, and at least one exogenous growth factor.

Suitable exogenous growth factors are selected from the group consisting of epidermal growth factor (EGF), basic fibroblast growth factor (bFGF), a combination of bFGF and EGF, and a combination of EGF and bFGF and platelet-derived growth factor (PDGF), or equivalents of each thereof.

The cells are cultured under low oxygen conditions for an effective amount of time. By culturing under "low oxygen conditions" is meant maintaining the oxygen concentration in the culture media at a level of from about 1% to about 6%. An effective amount of time intends that the cells have been cultured and passaged at least 7, or alternatively at least 8, or alternatively, at least 9, or yet further at least 10 times. In one aspect, the passaged cells are tested to verify that the multipotency of the cells is intact and are suitable for use in in vivo applications.

Non-limiting suitable primary sources for the cells for use in the disclosed methods include post-natal retinal tissue, including mammalian, e.g., murine, simian, leporidae and human adult tissue sources.

The cells and populations produced by the disclosed methods have therapeutic use and can be autologous or allogeneic to the host patient or recipient. Because the retinal progenitor cells are capable of differentiating into photoreceptor cells, they are useful to replace or repair photoreceptor tissue in a patient and, e.g., for the treatment of degenerative diseases of the eye such as retinitis pigmentosa, age-related macular degeneration and diabetic retinopathy.

The foregoing embodiments and aspects of the invention are illustrative only, and are not meant to restrict the spirit and scope of the claimed invention.

BRIEF DESCRIPTION OF THE DRAWINGS

The foregoing and other advantages and features of the invention will become apparent upon reading the following detailed description with reference to the accompanying figures and drawings.

FIG. 1A depicts a retina at 20 weeks gestational age, while FIGS. 1B-1E show various retina markers at 18 weeks gestational age. Scale bars are 100 um.

FIGS. 2A-2F are photomicrographs showing human retinal progenitor cells in culture expressing various progenitor and eye development markers in primary culture 3 days after isolation. FIGS. 2G and 2H show cell clumps and discrete cells dissociated and cultured after first passage. Scale bars are 200 um.

DETAILED DESCRIPTION OF EMBODIMENTS

Figure 1A:
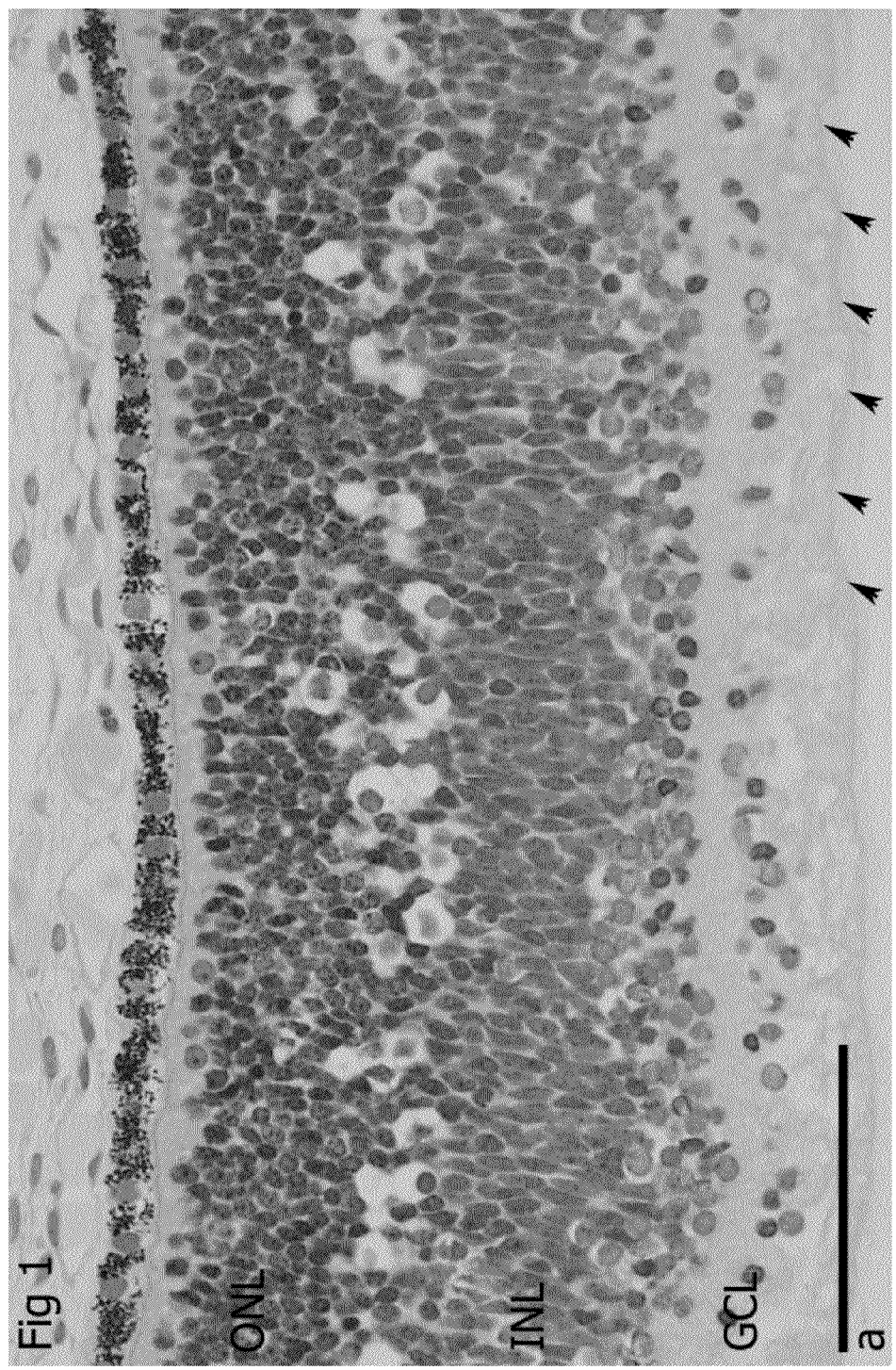
FIGS. 1A-1E are photomicrographs of a human fetal retina showing the morphology of the retina.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated, that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "host" or "patient" of this invention is an animal such as a mammal, or a human. Non-human animals subject to diagnosis or treatment are those in need of treatment such as for example, simians, murines, such as, rats, mice, canines, such as dogs, leporids, such as rabbits, livestock, sport animals, and pets.

The term "isolated" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. An isolated cell is a cell that is separated form tissue or cells of dissimilar phenotype or genotype.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. Pluripotent embryonic stem cells can be distinguished from other types of cells by the use of marker including, but not limited to, Oct-4, alkaline phosphatase, CD30, TDGF-1, GCTM-2, Genesis, Germ cell nuclear factor, SSEA1, SSEA3, and SSEA4. The term "stem cell" also includes "dedifferentiated" stem cells, an example of which is a somatic cell which is directly converted to a stem cell, i.e. reprogrammed. A clone is a line of cells that is genetically identical to the originating cell; in this case, a stem cell.

The term "propagate" means to grow or alter the phenotype of a cell or population of cells. The term "growing" or "expanding" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue. In yet another embodiment, the tissue is comprised of cardiomyocytes.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells. "Clonal proliferation" refers to the growth of a population of cells by the continuous division of single cells into two identical daughter cells and/or population of identical cells.

As used herein, the "lineage" of a cell defines the heredity of the cell, i.e. its predecessors and progeny. The lineage of a cell places the cell within a hereditary scheme of development and differentiation.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type or phenotype. "Dedifferentiated" defines a cell that reverts to a less committed position within the lineage of a cell. As used herein, the term "differentiates or differentiated" defines a cell that takes on a more committed ("differentiated") position within the lineage of a cell.

"Retinal progenitor cells", or "neuroretina-derived retinal stem cells", or "retinal stem cells", as those terms are used herein, are synonymous and mean isolated viable stem cells derived from neuroretinal tissue, such as the retinal neurosphere. The point of origin of these cells is one factor that distinguishes them from non-neural retinal cells, such as pigmented cells of the retinal pigment epithelium, the ciliary body or the iris. The cells of the invention are further distinguished by an inability to proliferate in the absence of growth factors. The cells of the invention can derived from either pre-natal or post-natal sources, and are capable of self-renewal, multipotency, and retina-specific differentiation into photoreceptors. Such cells are more particularly described in U.S. Pat. No. 7,514,259, the disclosure of which is incorporated by reference herein in its entirety. The retinal stem cells of the invention are capable of: (a) self-renewal in vitro; (b) differentiating into neurons and astrocytes (but not oligodendrocytes); (c) integrating into the neuroretina following transplantation to the posterior segment of the eye; and (d) differentiation into photoreceptor cells when grafted onto a retinal explant, or into the mature eye of a recipient.

As used herein in connection with the retinal progenitor cells of the invention, the term "multipotency", means the ability of the retinal progenitor cells to proliferate and form mature retinal cell types, particularly photoreceptor cells.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a preselected cell surface marker or other marker, e.g. myosin or actin or the expression of a gene or protein, A "biocompatible scaffold" refers to a scaffold or matrix for tissue-engineering purposes with the ability to perform as a substrate that will support the appropriate cellular activity to generate the desired tissue, including the facilitation of molecular and mechanical signaling systems, without eliciting any undesirable effect in those cells or inducing any undesirable local or systemic responses in the eventual host. In other embodiments, a biocompatible scaffold is a precursor to an implantable device which has the ability to perform its intended function, with the desired degree of incorporation in the host, without eliciting an undesirable local or systemic effects in the host. Biocompatible scaffolds are described in U.S. Pat. No. 6,638,369.

As used herein, the terms "treating," "treatment" and the like are used herein to mean obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder, e.g., macular degeneration. As is understood by those skilled in the art, "treatment" can include systemic amelioration of the symptoms associated with the pathology and/or a delay in onset of symptoms such as chest pain. Clinical and sub-clinical evidence of "treatment" will vary with the pathology, the individual and the treatment.

The terms "physiologic", or "physiologic oxygen", as used herein, refer to the low oxygen concentrations of the invention of from about 1% to about 6%, and the particularly preferred concentrations of from about 2% to about 4% as measured in the culture media. As is apparent to the skilled artisan, the oxygen level of the culturing device may be slightly higher in order to obtain the appropriate oxygen concentration in the media to which the cells are exposed.

The oxygen concentration in mammalian cell tissues in vivo typically varies from 0.5% for the retina to 19% for the upper airway epithelia. In the retina in particular, the adult retina oxygen concentration (or oxygen "tension") varies from about 0.5% for the inner nuclear layer to about 7% for the outer segments of the retina. For most cell cultures, the oxygen concentration is normally maintained at about 20%, the so-called "normaoxic" level. The term "anoxic", as may be used herein, refers to oxygen concentrations of less than about 1%.

A "composition" is intended to mean a combination of active agent, cell or population of cells and another compound or composition, inert (for example, a detectable agent or label) or active, such as a biocompatible scaffold.

A "pharmaceutical composition" is intended to include the combination of an active agent with a carrier, inert or active such as a biocompatible scaffold, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, Remington's Pharm. Sci., 15th Ed. (Mack Publ. Co., Easton (1975)).

An "effective amount" is an amount sufficient to effect beneficial or desired results. An effective amount can be administered in one or more administrations, applications or dosages.

Cells, Populations and Compositions

The invention relates to a process for producing an isolated population of multipotent retinal stem cells in vitro suitable for therapeutic use. The method requires culturing an isolated retinal progenitor cell under low oxygen conditions, typically wherein the oxygen concentration utilized in the culture media is from about 1% to about 6%, preferably from about 2% to about 4%. It has been found that the methods of the invention permit the expansion of human retinal progenitor cells in vitro, increase cell proliferation and multipotency marker expression, and decrease cell apoptosis. Importantly, the expanded cells of the invention maintain the ability to differentiate into specialized retinal cells, particularly photoreceptor cells.

Thus, in one aspect, the invention provides an in vitro method for preparing an isolated population of multipotent progenitor retinal progenitor cells, comprising culturing an isolated primary retinal progenitor cell under low oxygen conditions, wherein the low oxygen conditions comprise from about 1% to about 6% oxygen content of the culture medium, for an effective amount of time while maintaining multipotency of the cells, The isolated retinal progenitor cell to be cultured can be a primary retinal cell isolated from host tissue, e.g., a living host or a cadaver, prenatal sources, fetal tissue or adult tissue, and can be isolated from the retinal neurosphere. The cells can also be identified by markers, that include, for example, Otx2, Sox2, Pax6—eye field development transcription factors; CyclinD1, Ki67, hTERT—proliferative markers; cMyc, Klf4, Oct4—"stemness" transcription factors; SSEA4—surface antigen, characteristic for undifferentiated cells. Methods of screening for such factors are known in the art and described herein.

Culturing in low oxygen can be accomplished in more than one culture medium as described below. Prior to use, the cells can further be isolated from the medium and combined with an appropriate pharmaceutically acceptable carrier, non-limiting examples of which are described herein and known to the skilled artisan. In addition and prior to use, the isolated cells or cell populations can be further assayed for multipotency by screening, e.g., HIF1 alpha and HIF2 alpha as well as for the above-noted stem cell markers or independently or in combination with a telomerase assay as described below.

Suitable conditions for culturing include culturing in the presence of at least one growth factor as described herein and for at least 7, or alternatively at least 8, or further at least 9 or yet further at least 10 passages in low oxygen conditions.

The primary source of the cells can be from any suitable animal species as described herein. In one aspect, the primary retinal progenitor cells are isolated from post-natal retinal tissue, e.g., from the retinal neurosphere.

The expanded population of cells is further provided herein. Thus, in one aspect this disclosure provides an isolated population, e.g., an isolated substantially homogenous population of multipotent retinal cells produced by a method of one any of claims 1, 1b and 2-7.

According to the invention, isolated human retinal progenitor cells can be derived by the dissection of the human neural retina. During dissection, it may necessary to manage the highly tenacious vitreous gel component. This can be accomplished using a variety of techniques, alone or in combination, including vitrectomy, ocular inversion, mechanical resection and absorbent debridement, as well as enzymatic digestion. Suitable enzymes for this purpose include, but are not limited to, hyaluronidases and collagenases. It may also be advantageous to remove non-neural retinal tissue from the specimen used for retinal stem cell isolation. The non-neural tissue includes the optic nerve head and epithelium of the pars plana of the ciliary body, which is typically adherent along the peripheral margin (ora serrata). The tissue is preferably handled using aseptic techniques.

The isolated neuroretinal tissue can be mechanically macerated, and passed through a nylon mesh screen of about 100 micron pore size to dissociate the isolated neuroretinal tissue into cells. The use of a sterile small pore filter screen for the mechanical dissociation of the tissue permits the minimization of the use of enzymes that can degrade cell surface molecules such as growth factor receptors.

An aliquot of cells from the dissected tissue can then be placed in a culture vessel, such as a plastic tissue culture flask, which is preferably coated with a protein layer. Advantageously, the layer may be polyornithine overlaid with laminin or fibronectin.

The aliquot of cells can then be incubated, if preferred, in a first cell culture medium to provide an initial cell concentration for about 24 hours at about 35° C.-39° C., in low oxygen conditions (1% to 6%, preferably 2% to 4%, and most preferably 3% in the culture media). The first cell culture medium can include a physiologically balanced salt solution containing a D-glucose content of from about 0.5-3.0 mg/liter, preferably about 1 mg/liter, $N_2$ Supplement, and about 5-15% fetal calf serum, as well as 5-15% by volume neural/retinal-conditioned media and an effective amount of at least one antibiotic, such as gentamycin.

After about 24 hours of incubation in the first culture medium, that medium can be removed from the culture vessel. Then, a second culture medium that is essentially serum-free, is added to the culture vessel. The second culture medium can include a physiologically balanced salt solution containing a glucose content of about 0.5-3.0 mg/liter, preferably 1 mg/liter (e.g., DMEM/F-12 high glucose), $N_2$ Supplement, at least one growth factor at a concentration of about 30-50 ng/ml per growth factor, an effective amount of L-glutamine (about 0.5-3.0 mM, preferably about 1.0 mM), an effective amount of neural progenitor cell-conditioned medium, and an effective amount of at least one antibiotic, such as penicillin and/or streptomycin, in a low oxygen concentration as described previously. Advantageously, penicillin and/or streptomycin may be added as follows: 10,000 units/ml pen, 10,000 microgram/ml strep, added 1:50-150, preferably 1:100, for a final concentration of 100 units/ml, 100 microgram/ml, respectively, in the culture medium. Those of ordinary skill in the art reading this specification will appreciate that minor modifications can be made to the design of the culture media components and operating conditions.

The cell isolation and culture method of the invention can typically include the regular removal of non-viable cells and a portion of the culture medium from the culture vessel in which the cells are cultured, and replacing said portion with an equivalent amount of fresh, second culture medium. This culture maintenance step may be performed approximately every 2-7 days during the lifetime of the cell culture.

Maintenance of low oxygen conditions can be achieved using commercially available incubators with oxygen concentration control, or by placing culture flasks into chambers with manually controlled or digitally controlled temperature settings, humidity and concentrations of oxygen and carbon dioxide.

The survival and effectiveness of human retinal progenitor cells in vitro is influenced by numerous factors including the incorporation of various additives in the culture medium such as supplements, mitogens, serum and growth factors. In particular, the culture medium should include an exogenous growth factor to induce proliferation and survival in vitro. Effective exogenous growth factors include neurotrophins; mitogens; cytokines; growth factors; hormones; and combinations thereof, as will be appreciated by one of ordinary skill in the art. Advantageously, the culture medium includes one of the following growth factors or combinations of growth factors: epidermal growth factor (EGF), basic fibroblast growth factor (bFGF), a combination of bFGF and EGF, and a combination of EGF and bFGF and platelet-derived growth factor (PDGF) or an equivalent of each thereof.

Without being bound by theory, it has now been found that the maintenance of the cells, and the preservation of cell multipotency, is influenced by low oxygen concentration in the culture medium. While low oxygen concentration affects cell metabolism by several pathways, it has been found that the main mediators of cellular activity are the two Hypoxia Inducible Factors HIF1a and HIF2a (Hypoxia Inducible Factor 1 alpha and 2 alpha). These mediators are constitutively expressed but hydroxylated and ubiquitinated at oxygen concentrations of more than about 6%. Conversely, if the oxygen level is decreased, the HIF alpha subunits dimerise with the HIF beta subunit (ARNT), and the resulting complex is transported to the cell nucleus where it functions as a basic helix-loop-helix transcription factor.

HIF1 alpha expression is found in all types of cells. However, HIF2 alpha expression is limited to certain organs, such as the brain, heart, lung, kidney, liver, pancreas, intestine and retina. HIF1 alpha regulates metabolic pathways (shift to glycolysis), tissue remodeling (increase in metalloproteases and decrease in ECM production), migration (cheomokine expression), pro-survival pathways (for different cell types and oxygen tension: the HIF1a-ARNT complex may cause an increase in apoptosis via BNIP3, NIX, or a decrease in apoptosis by p53 inhibition and Epo activation), and genome methylation (3h3mCoenzA, JMJD1A). HIF2 alpha activates TGF alpha, the multipotency transcription factors Oct4, cMyc, Sox2, and Cyclin (D1, D2 and E2F) expression. Both HIF1a and HIF2a influence growth factor signaling.

The ability to significantly expand the number of cells to produce a population of multipotent retinal progenitor cells from an initial isolated population limited in size is critical for clinical studies involving such cells, as well as the eventual use of the cells for the treatment of degenerative ocular diseases using transplantation techniques. The current level of cell production achievable using conventional techniques is on the order of $10^9$ to $10^{10}$ cells for in vitro expansion of a single isolate. This level is generally inadequate for clinical use. It has now been found that this level of proliferation can be increased to $10^{18}$ to $10^{19}$ cells for each cell source by using low oxygen culture conditions in vitro.

In addition, it has also been found that the use of low oxygen culture conditions resulted in a doubling of the proliferation speed, thereby decreasing the accumulation of genome changes while promoting the positive selection for viable progenitors. These results are confirmed by the high levels of Ki67 and Cyclin D1 expression compared to passage 0 (isolation time point). The number of Ki67 expressing cells decreased significantly with passage in 20% oxygen conditions, but not in 3% oxygen conditions.

As indicated previously, the presence of both HIF (1 and 2) alpha isoforms was observed in human retinal progenitor cells. However, these markers play different roles in cell fate. HIF1 alpha primarily mediates hypoxic effects, while HIF2 alpha mediates the physiologic effects of low oxygen concentration. Hypoxic effects include stabilizing p53, blocking cell cycle progression and proliferation, and activating apoptosis. Physiologic effects include an increase in proliferation, multipotency gene expression, TERT upregulation, and cell cycle progression. HIF2 alpha is stabilized in human retinal progenitor cells at oxygen concentrations of 1% to 6%, and preferably from 2% to 4%, and this stabilization is maintained during cell passaging. Moreover, the functional properties of human retinal progenitor cells, including multipotency, are also stabilized.

Under normoxic conditions, the expansion of human retinal progenitor cells in vitro is linked to a loss in the ability of the cells to differentiate into mature cell types, such as photoreceptors and ganglion cells. However, under low oxygen conditions, human retinal progenitor cells have been shown to retain the ability to differentiate into photoreceptors.

Summarizing, the use of low oxygen conditions for culturing human retinal progenitor is beneficial and results in rates of proliferation double the rates for normoxic conditions, and further, the rates of cell proliferation are preserved at least through passage 16. For normoxic conditions, the cell proliferation rate reached a plateau at passages 5 and 6, while the use of low oxygen conditions showed only a small decrease in the proliferation rate. Further, cells expanded under low oxygen conditions have been shown to preserve their genomic integrity and multipotency properties. This also results in an increase in cell survival and integration stability following transplantation due to a switch to glycolysis, and the activation of pro-survival pathways and matrix metalloproteases.

Also provided by this invention are methods to genetically modify the isolated cell population by inserting or modulating the expression of one or more genes using methods known to the skilled artisan. In one aspect, such modification is achieved by transducing a polynucleotide encoding the gene into the source cell by any suitable method. For example, the polynucleotide of interest is inserted into a vector such as a viral vector which is then contacted with the cell under conditions that facilitate transfer of the vector and polynucleotide into the cell. The recipient cell is grown or propagated under suitable conditions to express the inserted gene. In other aspects, the cell is modified to enhance expression of the endogenous gene of interest. In further aspects, the genes are overexpressed as compared to a wild-type counterpart cell by inserting numerous copies of the polynucleotide or alternatively, enhancing expression of the endogenous gene of interest. Compositions and methods to reduce or block endogenous expression are also utilized. To promote expression, polynucleotides encoding the protein of interest can be introduced. To inhibit expression, polynucleotides or agents such as blocking antibodies, ribozymes, antisense polynucleotides or other inhibiting agents, can be introduced into the cell or population of cells.

Therapeutic Use

This invention also provides methods for replacing or repairing photoreceptor cells in a patient in need of this treatment comprising administering to the patient an effective amount of the isolated population or composition as described herein. In one aspect, the compositions and cell populations can treat or alleviate the symptoms of retinitis pigmentosa in a patient in need of the treatment by administering an effective amount of the populations or compositions. Further provided is a method for treating or alleviating the symptoms of age related macular degeneration in a patient in need of this treatment, comprising administering to the patient an effective amount of the isolated population or composition thereby treating or alleviating the symptoms of age related macular degeneration in said patient. For all of these treatments, the cells can be autologous or allogeneic to the patient. Patients include without limitation, mammals, such as murines, canines, felines, and human patients.

Administration of the cells or compositions can be effected in one dose, continuously or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents are known in the art. In a further aspect, the cells and composition of the invention can be administered in combination with other treatments.

Screening Assays

The present invention provides methods for screening various agents that modulate the differentiation of a retinal progenitor cell. For the purposes of this invention, an "agent" is intended to include, but not be limited to a biological or chemical compound such as a simple or complex organic or inorganic molecule, a peptide, a protein (e.g. antibody), a polynucleotide (e.g. anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated, that the agent is used alone or in combination with another agent, having the same or different biological activity as the agents identified by the inventive screen.

To practice the screening method in vitro, the isolated population of cells is obtained as described above. When the agent is a composition other than a DNA or RNA, such as a small molecule as described above, the agent can be directly added to the cells or added to culture medium for addition. As is apparent to those skilled in the art, an "effective" a mount must be added which can be empirically determined. When the agent is a polynucleotide, it can be directly added by use of a gene gun or electroporation. Alternatively, it can be inserted into the cell using a gene delivery vehicle or other method as described above. Positive and negative controls can be assayed to confirm the purported activity of the drug or other agent.

The invention may be further described and illustrated in the following examples which are not in tended to limit the scope of the invention thereby.

EXAMPLES

Materials and Methods

Retina Morphology

The morphology of the neural retina at 20 weeks gestational age was investigated. One eye cup was fixed in Karnovsky fixative, embedded in plastic and cut (2 um thick) with H&E staining One eye cup was fixed in 4% PFA, embedded in OCT, cryosectioned (6 um thick) with further immunohystochemistry for Ki67, Sox2, Pax6, Recoverin, beta3-tubulin, laminin, Opsin Red/Green, Opsin Blue, Rhodopsin, Calbindin and mGluR6.

Cell Isolation hRPCs (human retinal progenitor cells) were isolated as described, with small modifications, in the following references: Klassen, H. J. et al., *Multipotent Retinal Progenitors Express Developmental Markers, Differentiate into Retinal Neurons, and Preserve Light-Mediated Behavior*, Invest. Opthalmol. Vis. Sci., 2004, 45(11), pages 4167-4173; Klassen, H. et al., *Isolation of Retinal Progenitor Cells from Post-Mortem Human Tissue and Comparison with Autologous Brain Progenitors*, J. Neuroscience Research, 2004, 77(3), pages 334-343; Klassen, H. et al., *Progenitor Cells from the Porcine Neural Retina Express Photoreceptor Markers after Transplantation to the Subretinal Space of Allorecipients*; Stem Cells, 2007, 25(5); pages 1222-1230. Briefly, whole neuroretinas from human fetal eyes (16-20 weeks gestational age) were dissected, dissociated in 0.1% collagenase I (Sigma) during 4 cycles (1.5 hour of fermentation in total), and plated in modified Ultraculture media (10 ng/ml rhEGF, 20 ng/ml rhbFGF, Pen/strep, Nystatin and L-glutamine) or frozen. The amount and viability of single cells and clumps were estimated using Trypan blue and a haemocytometer.

Cell Culture

Cells were plated at a density of approximately 10,000 cells/cm$^2$ and cultured under either physiologic oxygen (3% oxygen) or normoxic (20% oxygen) conditions at 37° C., 100% humidity, 5% $CO^2$ in modified Ultracutlure media (10 ng/ml rhEGF, 20 ng/ml rhbFGF, Pen/strep, Nystatin and L-glutamine) on flasks coated with bovine serum fibronectin (Akron). Cells were passaged at 75%-85% confluence (usually each 2-5 days) using Trypsin-EDTA solution. At each passage, the cells were counted and plated at the density mentioned above. Low-oxygen conditions were created in a Thermo 150i incubator, not exceeding the limit of 6% oxygen.

Cell Proliferation and Growth Curve

Cell proliferation in both conditions was assessed during routine passaging by cell count via a haemocytometer (at least in two flasks for each passage/source). CyQuant NF assay (Invitrogen) was performed to estimate proliferation speed on each passage: a calibration curve was built by plating 1000, 2000, 4000 and 8000 cells in wells of a 96-well plate (BD Optilux). The amount of cells in experimental wells (4000 cells/well) was assessed by CyQuant staining after 48 and 72 hours (n=4 for calibration curve and n=6 for experimental wells).

Apoptosis hRPCs (p1-p9) for TUNEL assay (Roche) were plated in 16-well slides coated with fibronectin, the same way as for maintenance conditions (4,000 of alive cells in each well, hRPC media with supplements); 48 hours after plating cells were fixed, permeabilised (0.01% Triton-X, 0.01% sodium citrate), and stained for double-stained DNA breaks. Slides were mounted, and a cell count was performed in 9 fields of view for each condition. Western blot analysis for pro-survival pathway proteins p44/42 and p38 (Cell Signaling) was performed for passages 1, 5 and 10 in both conditions (protein was collected after 4 days in culture).

Immunocytochemistry

Cells were assessed via immunocytochemical analysis at passages 1, 3, 5, 7 and 10 in both conditions, and on passage 16 in 3% oxygen for sternness and proliferation marker expression: Otx2, Sox2, Pax6—eye field development transcription factors; CyclinD1, Ki67, hTERT—proliferative markers; cMyc, Klf4, Oct4—"stemness" transcription factors; SSEA4—surface antigen, characteristic for undifferentiated cells. For this purpose, 4,000 cells were plated in each well of 16-well fibronectin coated chamber glass slides (Nunc). After 24 hours of incubation under appropriate conditions, cells were washed in PBS, fixed (cold, freshly prepared 4% PFA), permeabilised (0.02% Triton X-100 in 5% BSA), blocked and stained with primary antibodies overnight at 4° C., and secondary antibodies (1:50, Goat Cy3-conjugated anti-rabbit or anti-mouse, Jackson Immunoresearch) for 1 hr at room temperature.

Western Blot hRPCs cultured under the conditions described above (3% and 20% oxygen) for 4 days were harvested for protein analysis on passages 1, 3, 5, 7, 10 and 16, lysed in RIPA buffer, and analyzed for protein expression by Western blot. Proteins were separated on 8% SDS-PAGE gel, transferred to a PVDF membrane (Bio-Rad), which was blocked with 5% non-fat milk (Bio-Rad) in TBS-T, and stained with antibodies diluted in 5% BSA in TBS-T (EGFR, HIF1alpha, HIF2alpha, hTERT, Nestin, Sox2, Oct4, Klf4, cMyc, p44/42, and p38). Resulting bands were imaged with ECL Plus (Perkin Elmer) and CL-Xposure film (Thermo Sientific). Anit-bActin HRP-linked antibodies (Abcam) were used as a loading control. Band square was measured using ImageJ.

Telomerase Activity Assay

Telomerase activity was assessed in both experimental conditions on passages 1, 3, 5, 7, 10 and 16 by the TRAPeze method according to the manufacturer's (Millipore) instructions. Briefly, cells were harvested, lysed in CHAPS buffer for 30 minutes on ice, and the telomers were amplified for 30 minutes at 30° C. The products were amplified using Platinum Taq (Invitrogen), separated by PAGE gel electrophoresis (non-reducing conditions) and stained with SYBR Gold (1:10000, Invitrogen) for 20 minutes at room temperature.

Differentiation Abilities In Vitro

To assess the ability of hRPCs to differentiate in vitro, hRPCs expanded in 3% oxygen were plated from passages 1, 5, 10 and 16 on fibronectin & laminin-coated 16-well slides. The cells were cultured in differentiating media (DMEM/F12, 1XNEAA, L-glu, 5% HI FBS, Pen/strep and Nystatin) in 3% oxygen. On days 2, 5 and 9, cells were fixed and stained for blue opsin (short-wave cones), red/green opsin (long-wave cones), rhodopsin (rods), recoverin (photoreceptor precursor), calbindin (horizontal cells), GFAP (Muller & ganglion cells), Glutamine sythetase (ganglion cells), MAP2 and Cyclin D3 (gangion cells) and PKCa (bipolar cells). The same staining was performed for hPRC on the same passages but after 24 hours in maintenance conditions. The ability to differentiate was estimated by comparing the number of cells expressing mature retinal markers in differentiating versus maintenance conditions.

Results

Eye Morphology

The human neural retina at 20 weeks gestational age is 250 um thick, compared to 500 um thick for an adult retina. Three layers of the retina can be distinguished at this age. The ganglion cell layer is separated from the others by the inner plexiform layer, while the inner and outer nuclear layers only start to diverge. An outer plexiform layer is not present at this stage of development. Due to the absence of rods and cones outer segments, the outer limiting membrane is not present, while the space between the ganglion cell layer and inner limiting membrane is wider than the inner plexiform layer. See FIG. 1A, which shows that the outer and inner nuclear layers are not completely separated, with outer segments not present, while the inner limiting membrane (arrows) and ganglion layer have been formed.

Figures 1B, 1C:
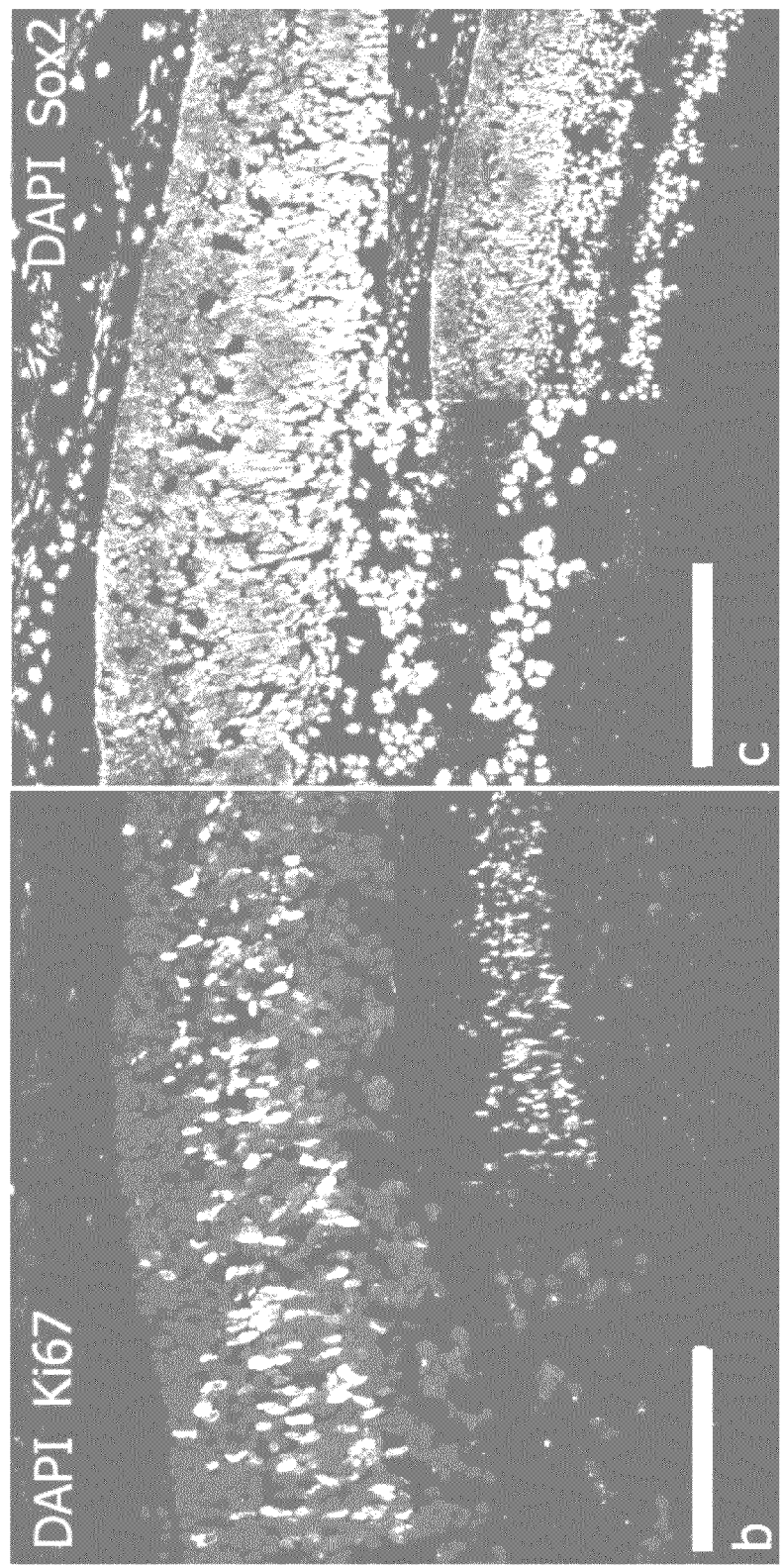
Figures 1D, 1E:
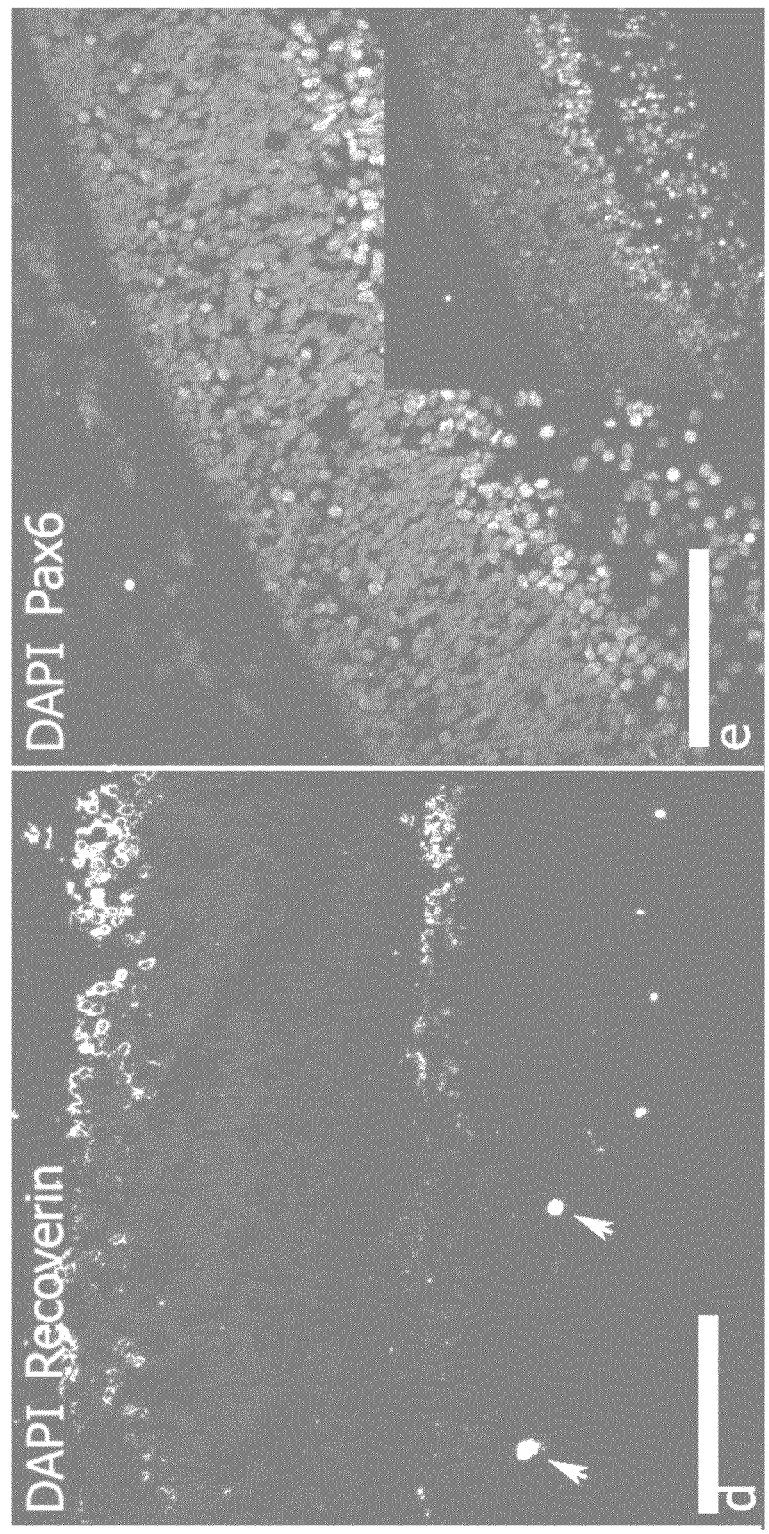

At 18 weeks gestational age, the innermost portion of the ganglion cell layer is presented by single, recoverin-positive cells. Signs of developed photoreceptors (staining for Blue and Red/Green opsins, rhodopsin, outer segments showed negative) have not been found, which makes neural retina at this age good for precursor isolation. Recoverin expression was limited by several cell layers within the outer nuclear layer and single cells (possibly photosensitive ganglion cells) in the ganglion cell layer. Ki67 is present in the middle of the conglomerate of inner and outer nuclear layers—but not in the layers, expressing recoverin. Sox2 is expressed in all cells within the neural retina, but at low levels in cells close to the outer limiting membrane. FIG. 1B shows proliferative marker Ki67 present in the middle of the inner and outer nuclear layers, but not in the layers, expressing recoverin. FIG. 1C shows neural progenitor marker Sox2 expressed in all cells within the neural retina, with slightly decreased levels in the outer nuclear layer. FIG. 1D shows that recoverin (photoreceptor precursor marker) expression was limited to the outer nuclear layer and single cells in the ganglion cell layer. FIG. 1E shows that the Pax6 marker is present in both the outer and inner nuclear layers.

Cell Isolation and Cell Culture

It was found that hRPC isolation can be performed up to 24 hours after enucleation. From each pair of eyes we can obtain 17.8 mln (+/−1.5 mln) single cells (with viability of 52%+/−16% mln) and 1.5 mln (+/−0.5 mln) clumps, consisting of 10-100 cells. The clump viability, indirectly assessed by adhesion to fibronectin during the first hour after plating, was about 70% and does not vary between two conditions. Cell and clump viability does not decrease greatly after freeze/thaw. Most of the small single cells, isolated from the retina, die on the second-third day after plating, and most of the primary pool was obtained from the clumps outgrowth. FIG. 2H shows the clumps. After the first passage, cells slightly increased in size but kept high nucleus/cytoplasm ratio, obtain triangle or spindle morphology and the culture became more homogeneous. FIG. 2G shows dissociated and cultured cells becoming more homogeneous, obtaining higher levels of Ki67 expression, losing recoverin and increasing in size.

The ratio of Ki67 and Pax6 expressing cells in culture was approximately the same as in the retina prior to isolation, but much lower than during further passaging. The ratio of recoverin-positive cells was decreased, and the cells did not survive further passaging, while the rate of Sox2 expression increased, which suggests a sort of positive selection for progenitors (Sox2) and a negative selection for late precursors (recoverin). Despite some reports that cell adhesion decreases in low oxygen conditions due to Integrin downregulation, no differences were observed in hRPC adhesion to fibronectin-coated (75 ug/ml) culture surfaces. As shown earlier, proper adhesion is critical for survival and expansion of these cells. In specified maintenance conditions, hRPC cells remain unchanged until passages 3-4 in regular oxygen conditions, and passages 9-10 in low oxygen conditions, while their morphology flattened. FIG. 2A shows that Ki67 expression in primary culture was low compared to further passages. FIGS. 2B and 2C show that Pax6 and Otx2 were expressed only in come cells, while FIG. 2D shows that recoverin was expressed in some positive cells. FIG. 2F shows that Sox2 was expressed in most of the cultured cells.

Cell Proliferation and Growth Curve

The rate of hRPC proliferation in 20% oxygen was constant during the first 4-5 passages (depending on the cell source), reaching a plateau at passages 5-6 (about 20 days in culture). This data is shown in FIG. 1 which graphs the growth kinetics of human retinal progenitor cells as the number of cell divisions vs. time (days) for 3% oxygen and 20% oxygen. After "exiting" the plateau, which took about 10 days, the growth rate in 20% oxygen decreased compared to earlier passages. A "negative gain" in CyQuant Assay on passages 8-9 in 20% oxygen can be explained by the increase in the apoptosis level. In 3% oxygen, a slight decrease in the proliferation rate after the first 5 passages (12 days in culture) was observed, but the population double time remains at a level lower than 1.5 days up to and including passage 16 (the point at which the experiment ended).

Figure 3:
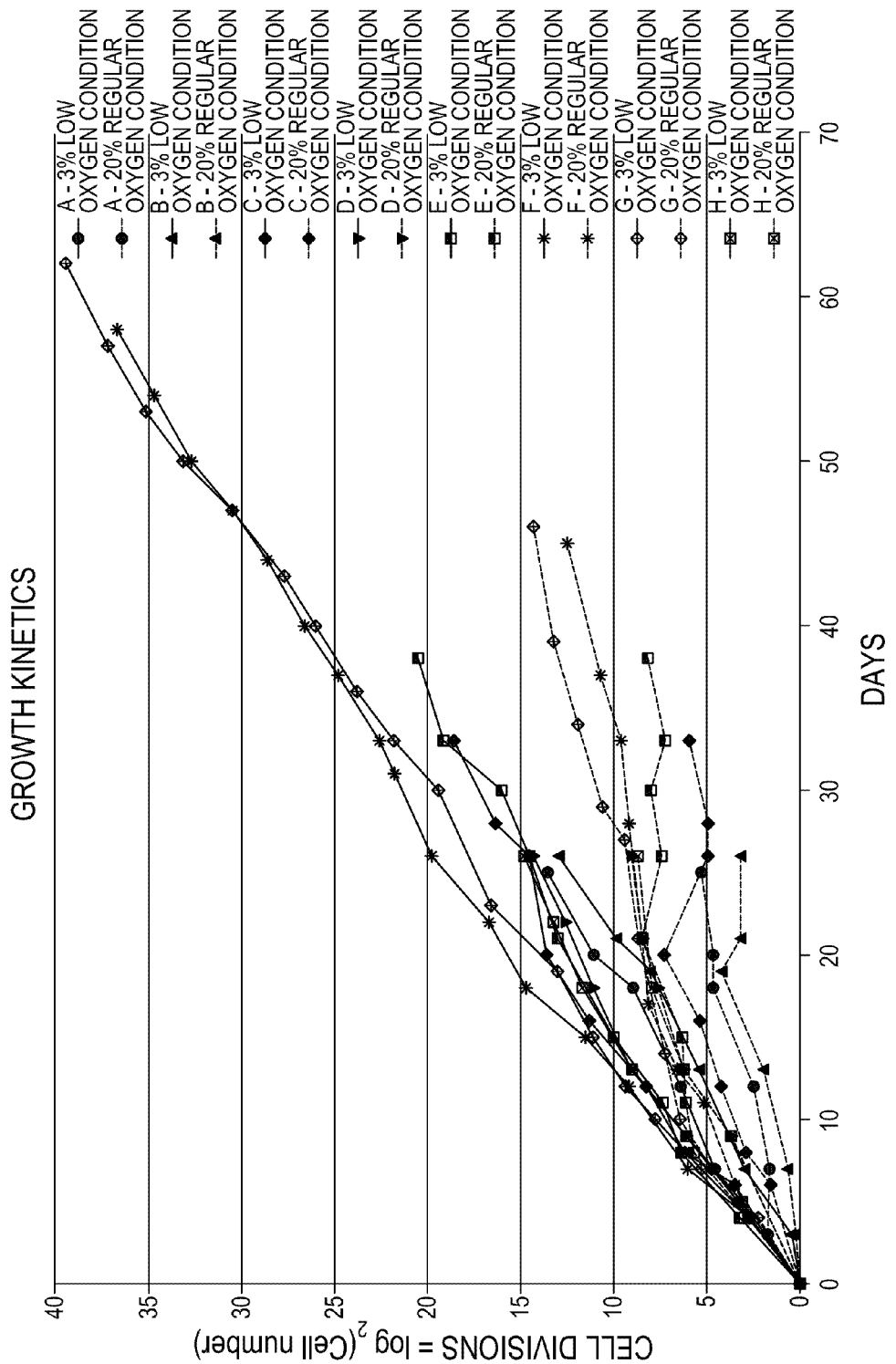
FIG. 3 is a graph comparing the growth kinetics for human retinal progenitor cells for both low oxygen cell culture conditions and normal oxygen cell culture conditions.

FIG. 3 is a graph showing the growth kinetics of human progenitor cells. The estimated size of the hRPC population, expanded in both low and regular oxygen conditions, is established for each of the 8 different sources. The points on the graph represent the passaging procedure when cells were counted (at least twice for each source/passage).

Proliferative Markers

Figure 4A:
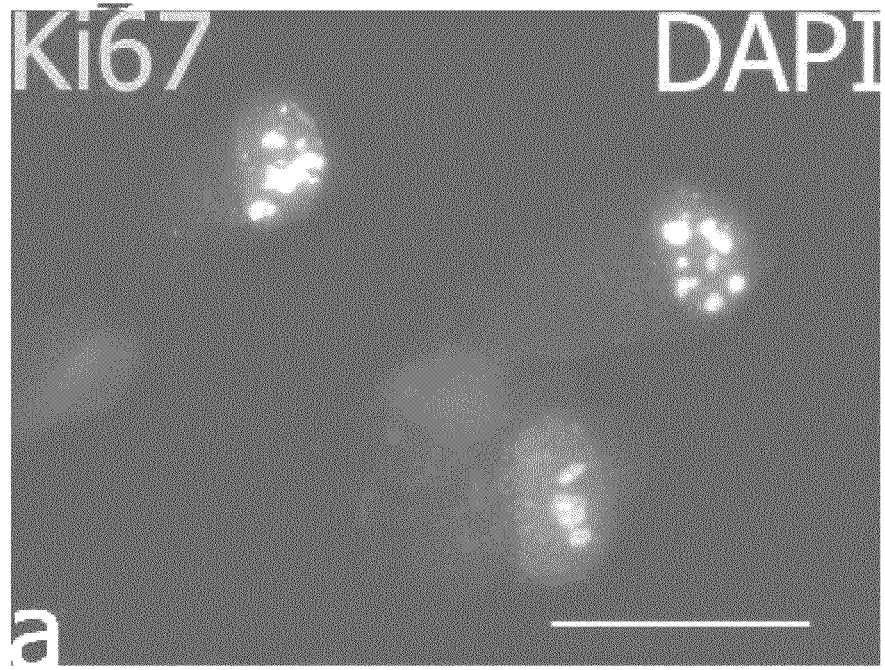
FIGS. 4A-4D are photomicrographs and bar graphs showing proliferative marker Ki67 and cell cycling marker CyclinD1 expression in low and regular oxygen conditions for passages 1, 3, 5, 7, 10 and 16 (only for low oxygen).
Figure 4B:
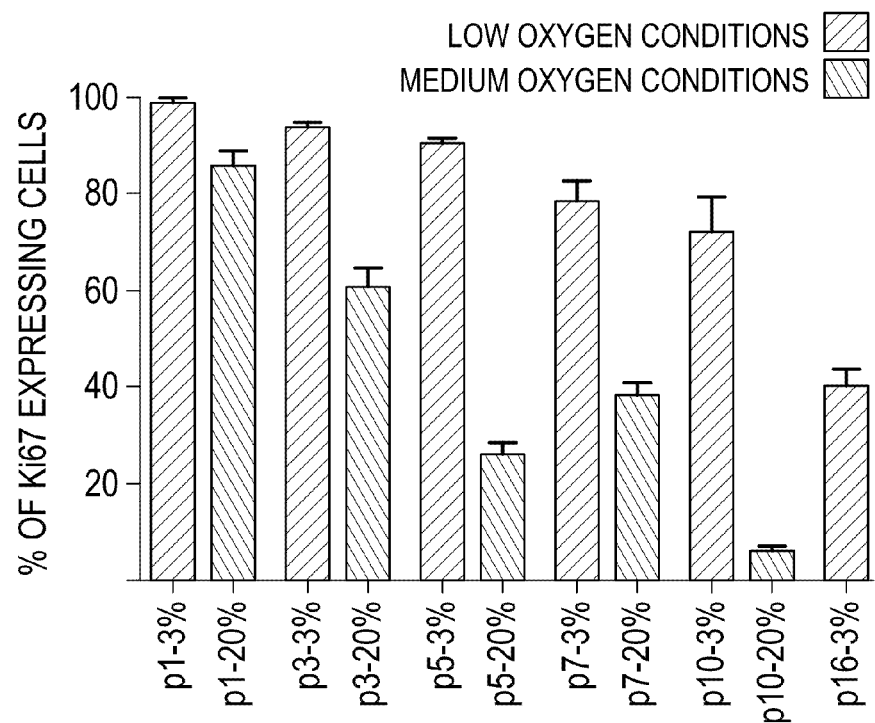
Figure 4C:
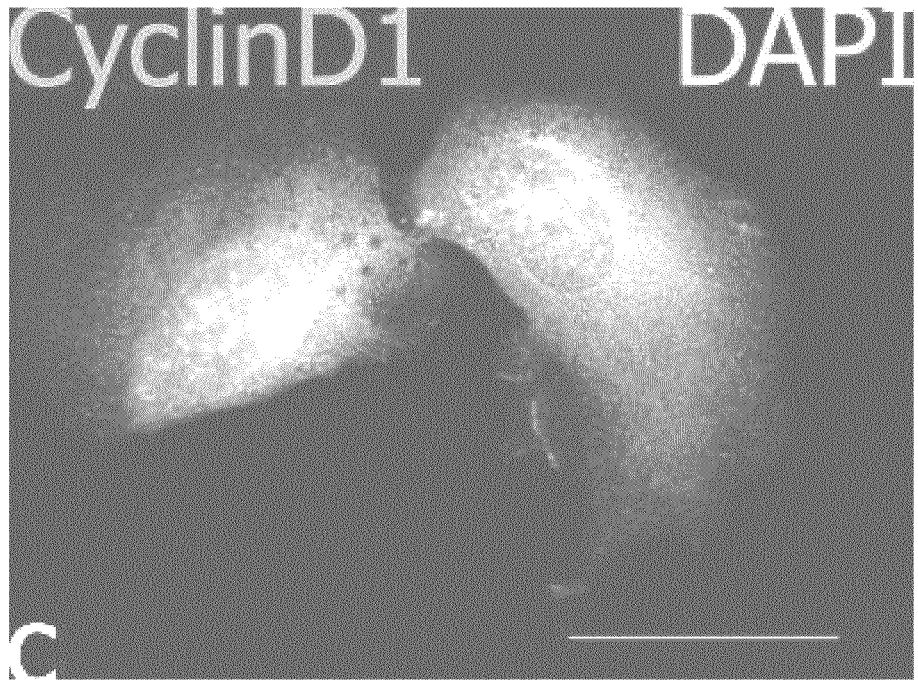
Figure 4D:
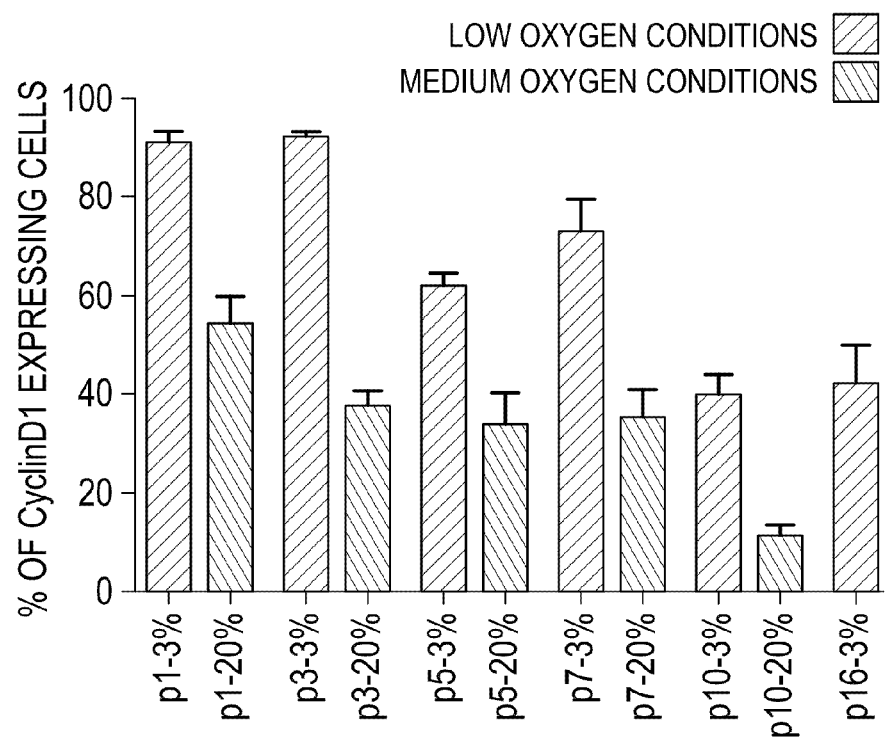
Figure 4E:
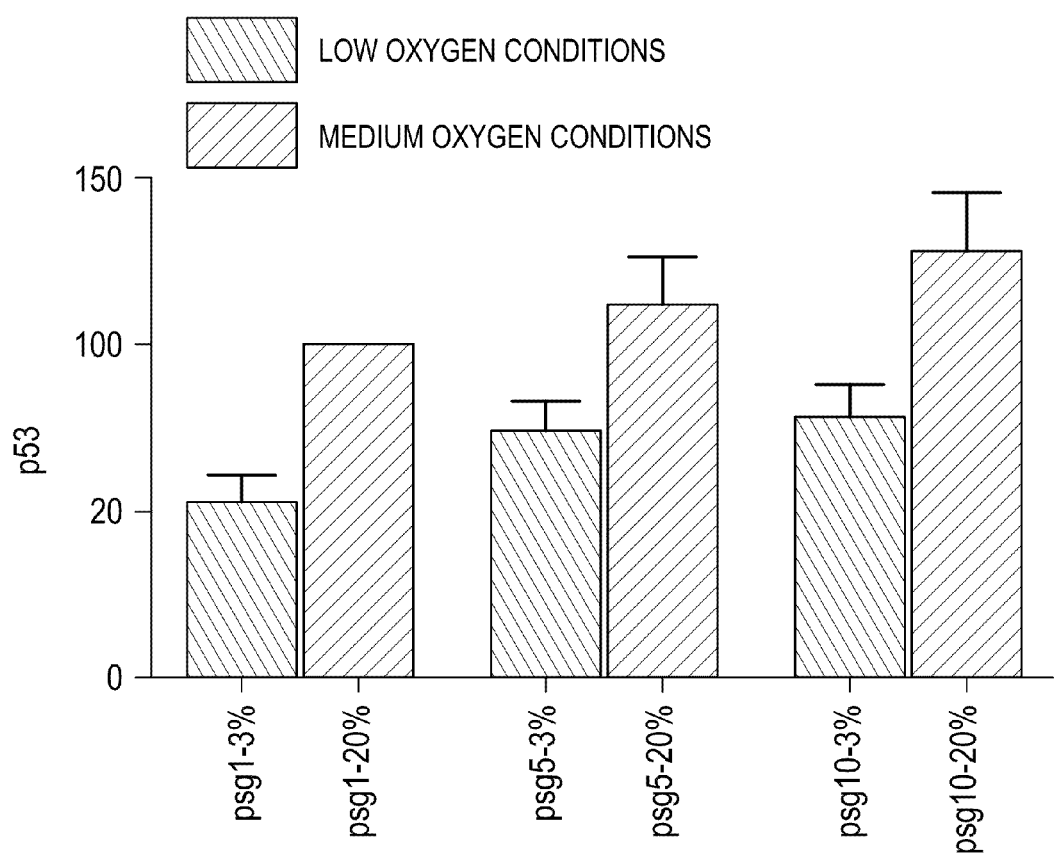
FIG. 4E is a bar graph showing cycle checkpoint protein p53 expression in regular oxygen conditions. Scale bars are 50 um.

The observed increase in hRPC proliferation in 3% oxygen conditions correlates with the increase in expression of markers Ki67 and CyclinD1. An increase in p53 expression at all passages in normoxia conditions compared to hypoxia conditions was also observed. See FIGS. 4A-4D which depict photomicrographs and bar graphs for proliferative marker Ki67 and cell cycling marker CyclinD1 expression in low and regular oxygen conditions for passages 1, 3, 5, 7, 10 and 16 (only for low oxygen). FIG. 4E is a bar graph showing that cycle checkpoint protein p53 expression is higher in regular oxygen conditions.

Apoptosis

The increase in p53 expression together with growth kinetics on passages 8 and 9 is linked with the higher apoptosis levels in 20% oxygen conditions as determined by the TUNEL assay. It does not exceed the 2% level in the hypoxia group at passages 1-7, and increased to 5% at passage 8. In the normoxia group, it increased from the 2% level on passage 1 to 6% on passages 5, 6, and 7, and on passage 8 it reached 20%. The variability between cell sources in the number of TUNEL-positive cells was also higher in the normoxia group. The "pro-survival" effect of hypoxia was also supported by the observation that after trypsinization and freeze/thawing hRPCs in 3% oxygen conditions havw higher vialbility (less floating cells). The same low oxygen anti-apoptotic protection was shown in vitro and in vivo in different cell types via activation of pro-survival pathways.

Figure 5A:
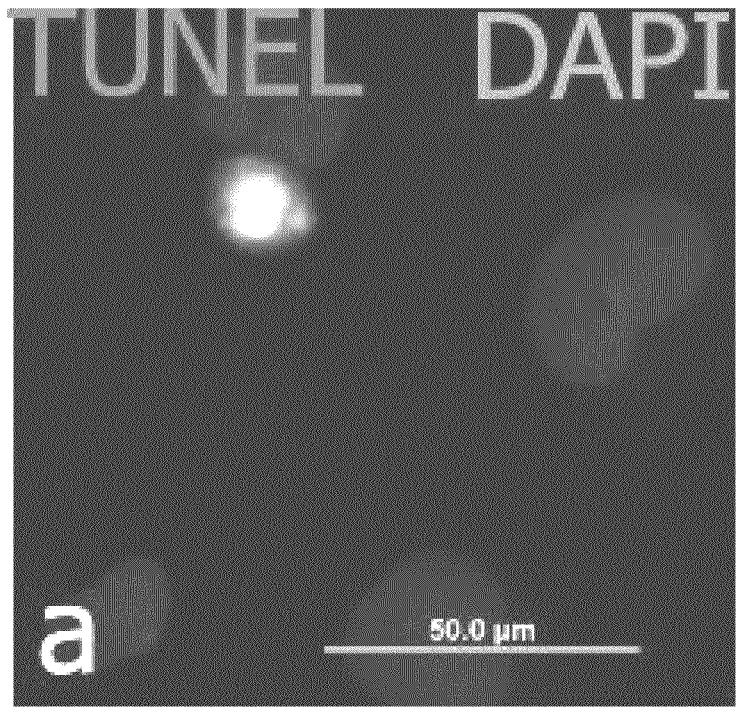
FIGS. 5A and 5B are a photomicrograph and a bar graph showing the ratio of apoptotic cells in low and regular oxygen culture conditions on passages 1-9. Scale bar is 50 um.
Figure 5B:
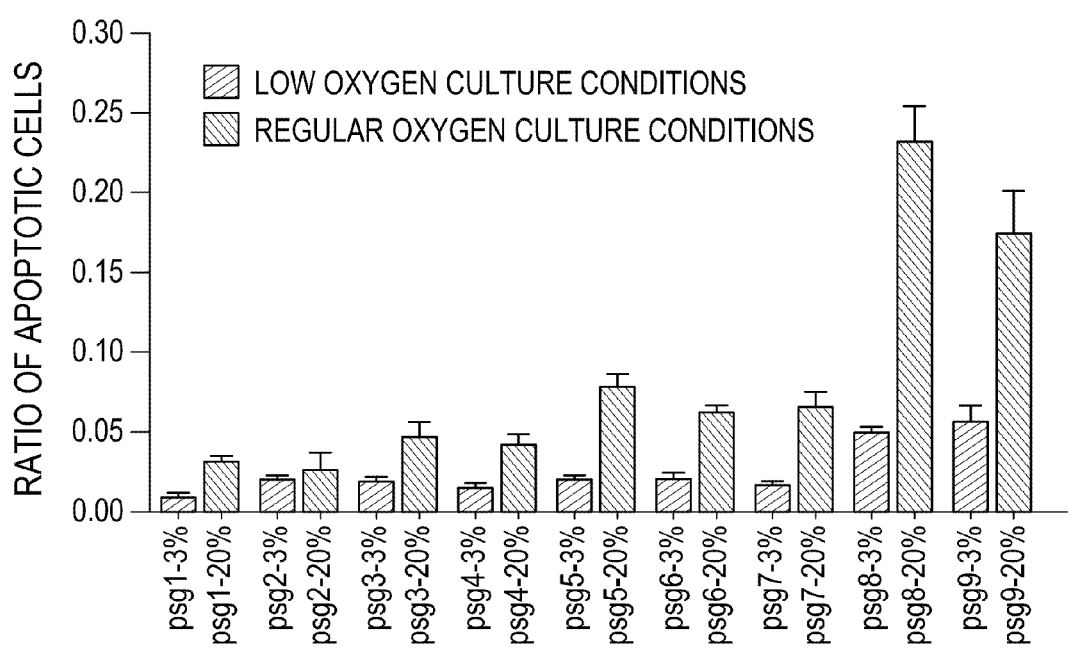

FIGS. 5A and 5B are a photomicrograph and a bar graph showing the ratio of apoptotic cells in low and regular oxygen culture conditions on passages 1-9. Although not wishing to be bound to any specific explanation or theory of operability, a possible mechanism for this result is the upregulation of p39 and/or p44/42 in 3% oxygen.

Telomerase Expression and Activity

Figure 6:
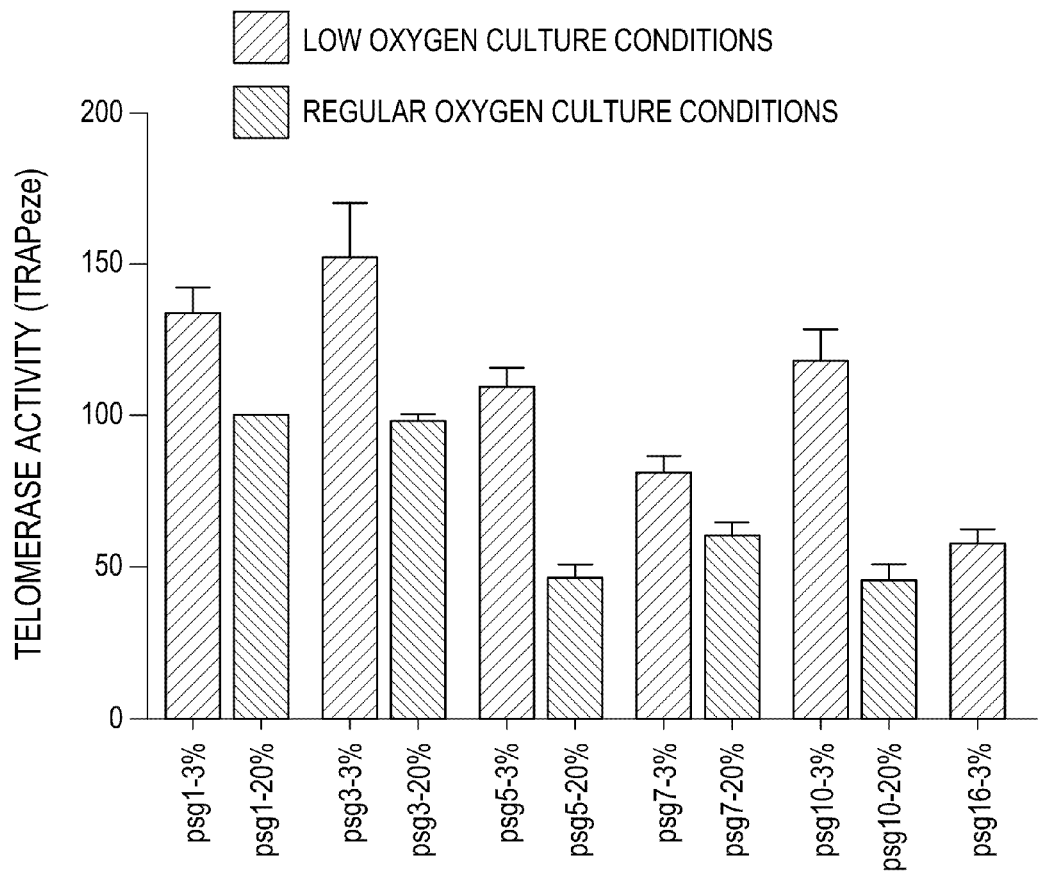
FIG. 6 is a bar graph of relative telomerase activity in hRPCs obtained for passages 1, 3, 5, 7, 10 and 16 for low and regular oxygen conditions.
Figure 7A:
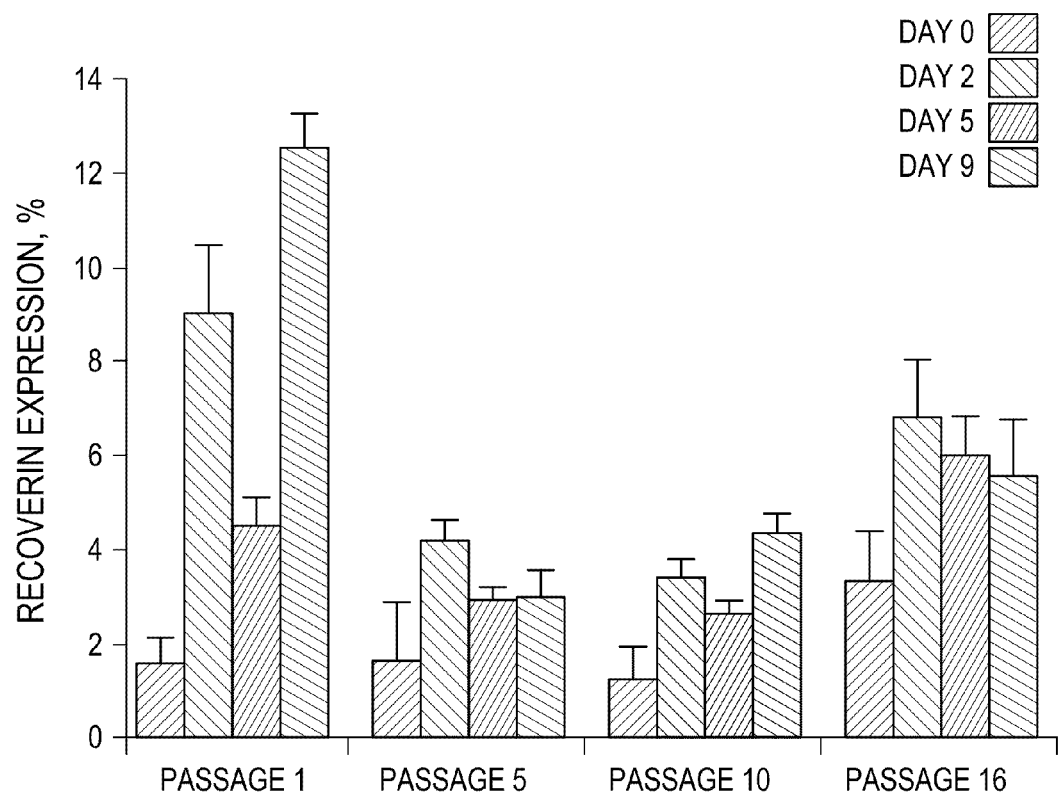
FIGS. 7A-7E are a series of bar graphs showing the ratio of cells expressing specialized photoreceptor retinal cell markers in maintenance conditions and at 2, 5 and 9 days post-differentiation on passages 1, 5, 10 and 16.
Figure 7B:
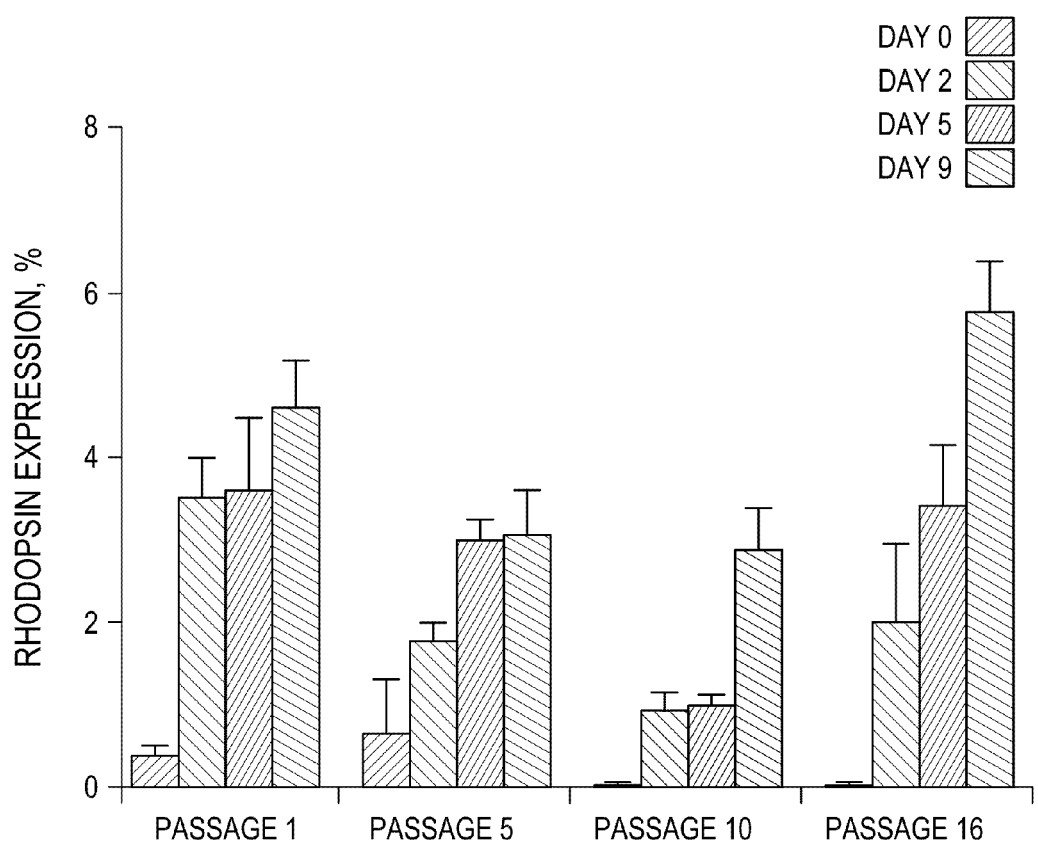
Figure 7C:
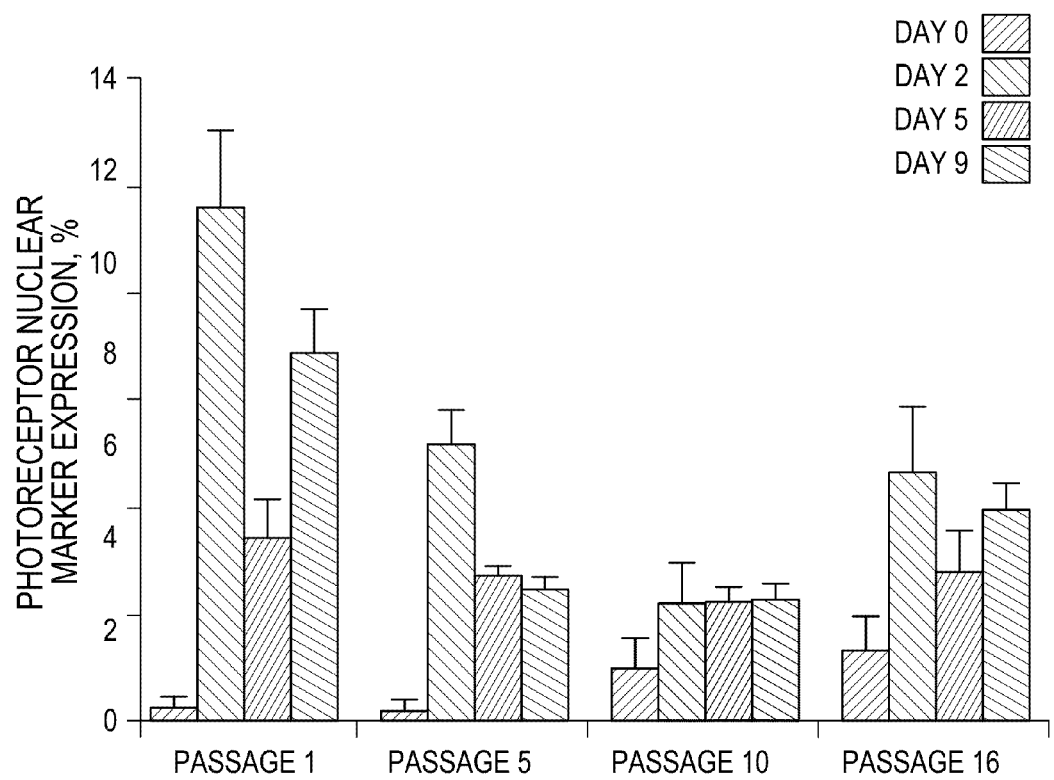
Figure 7D:
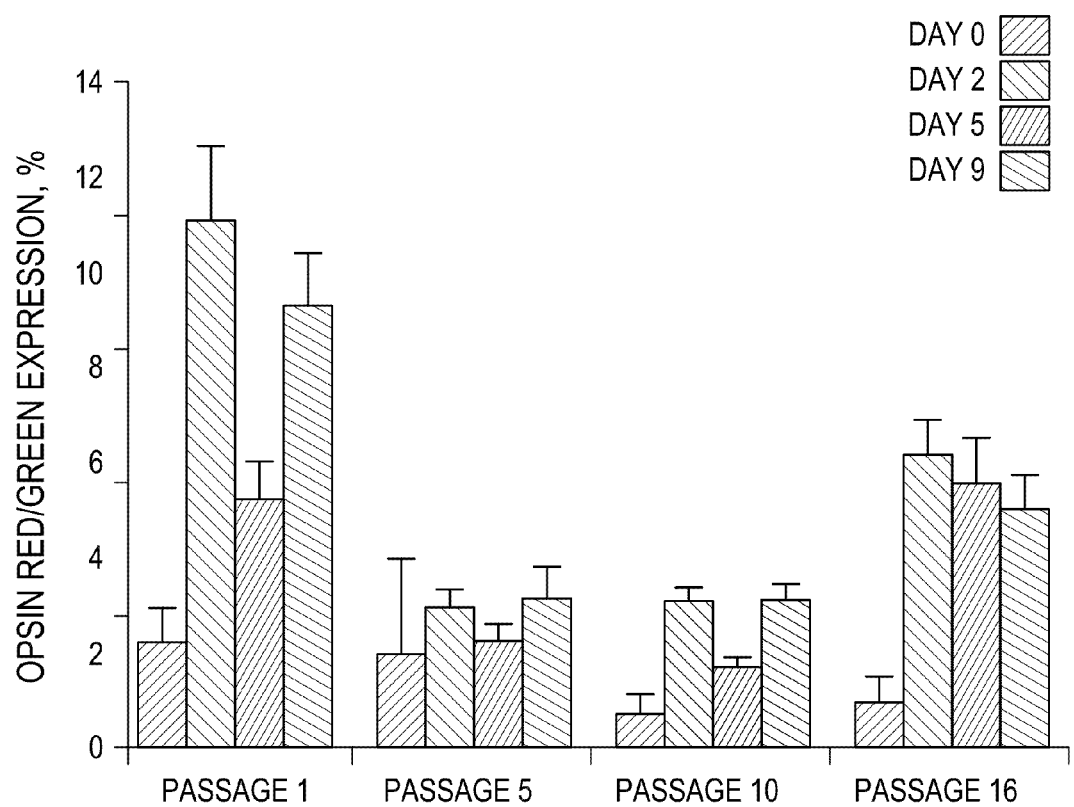
Figure 7E:
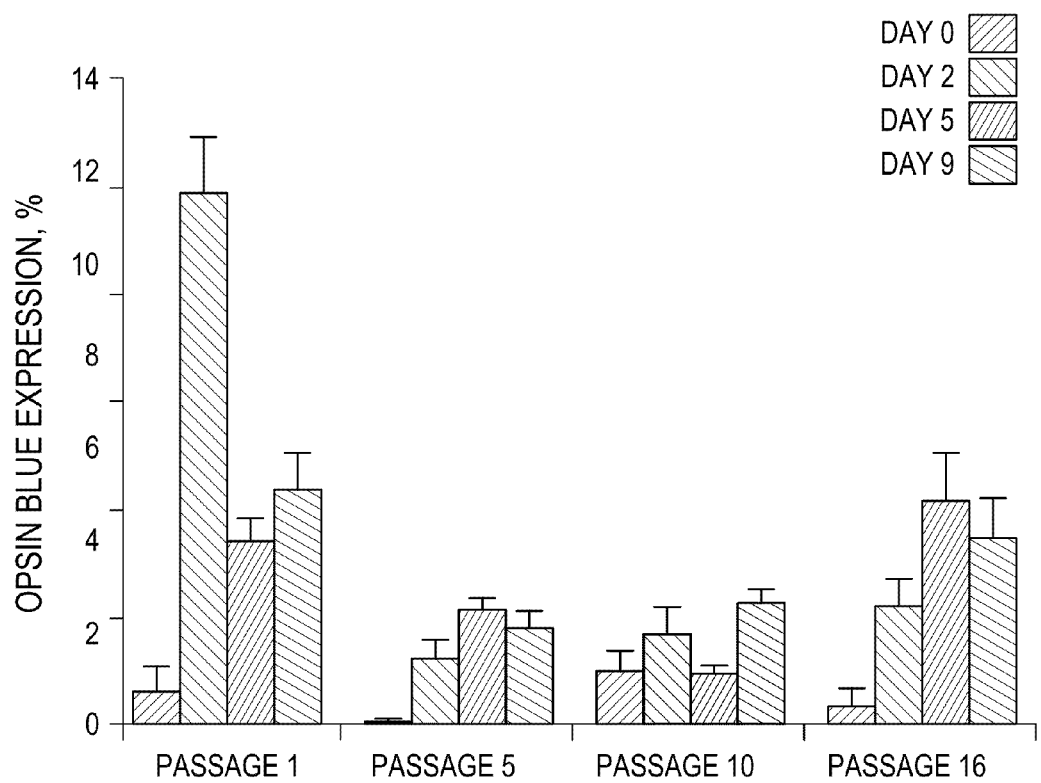
Figure 8A:
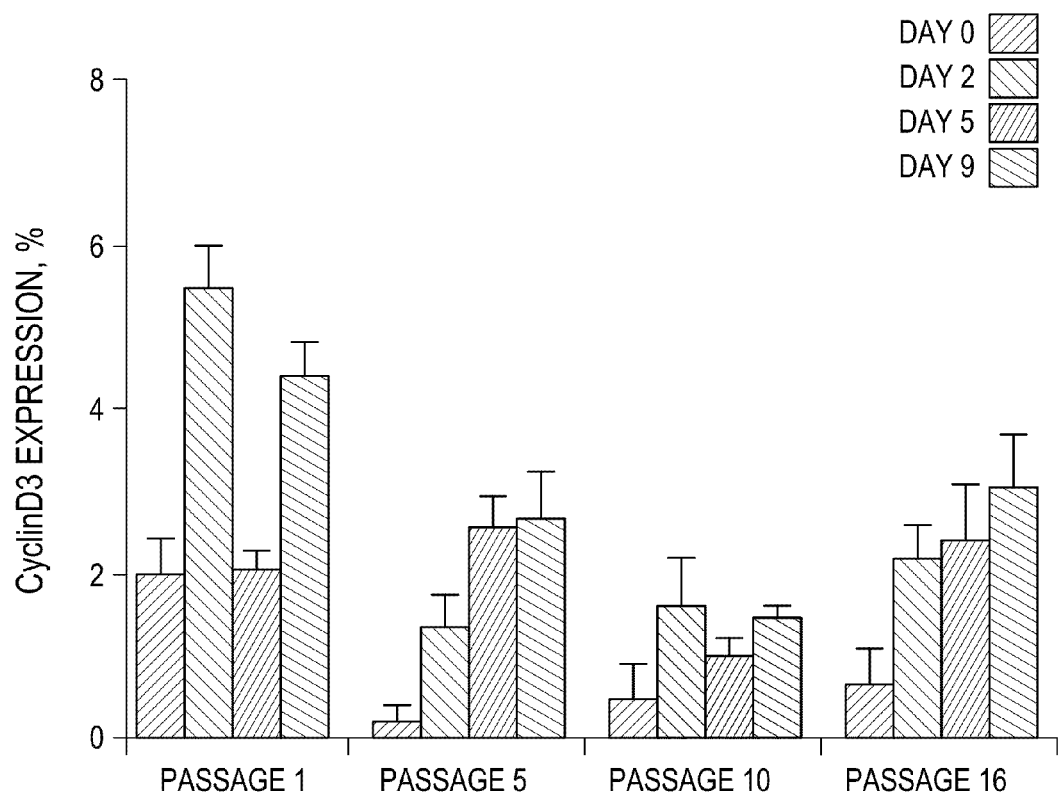
FIGS. 8A-8F are a series of bar graphs showing the ratio of cells expressing specialized retinal cells markers in maintenance conditions and at passages 1, 5, 10 and 16.
Figure 8B:
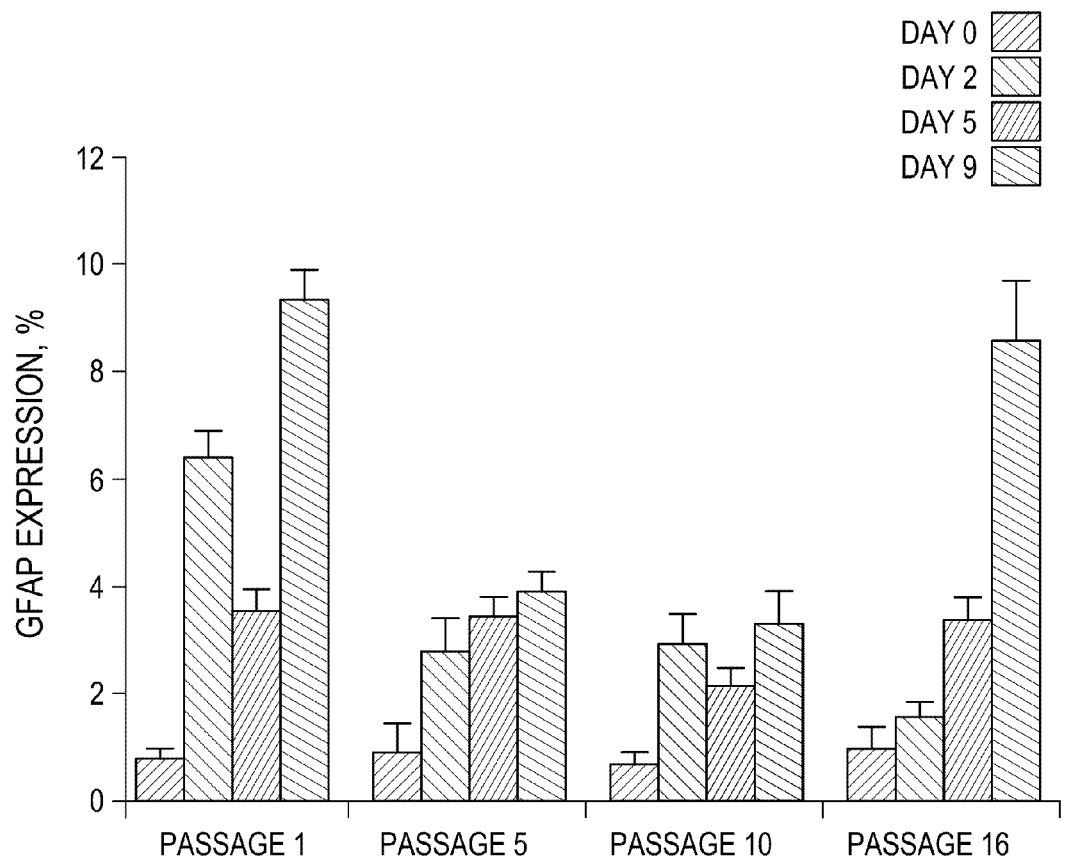
Figure 8C:
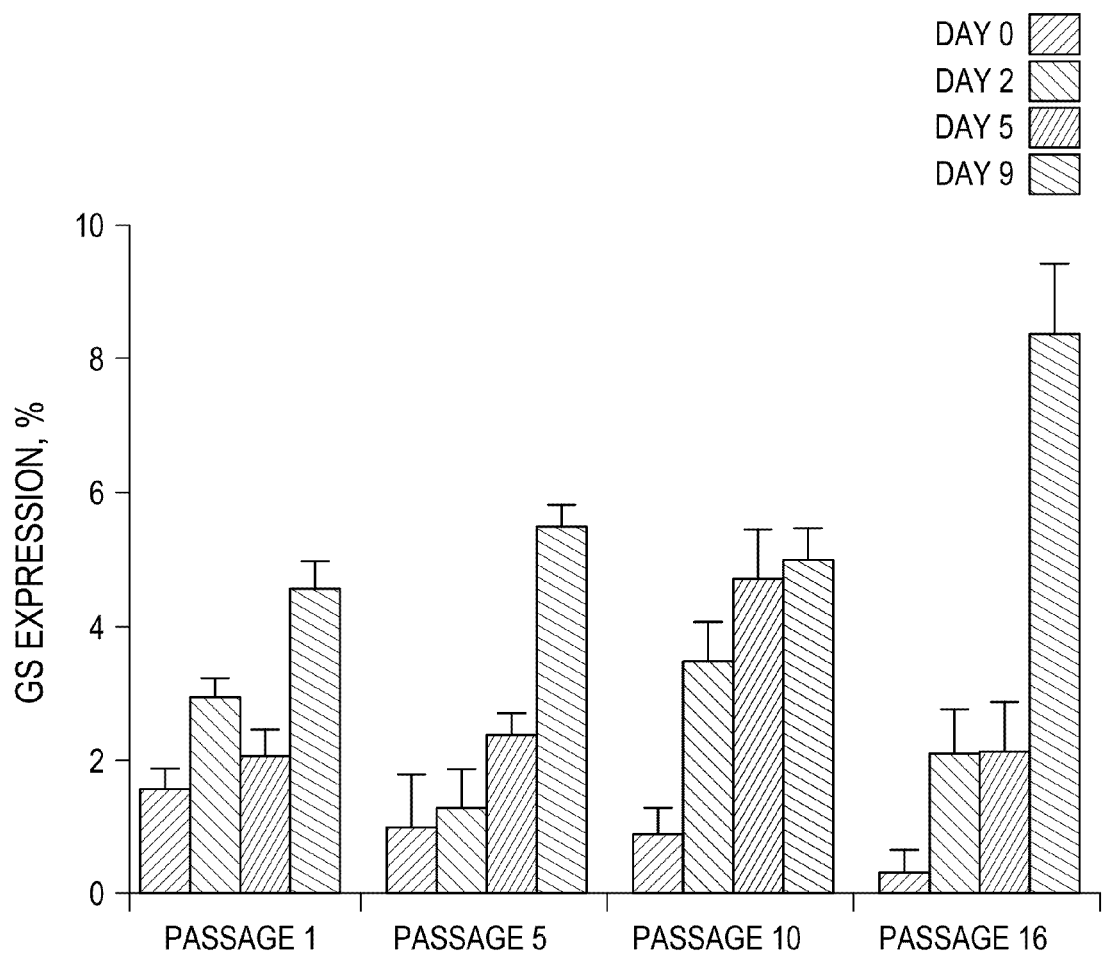
Figure 8D:
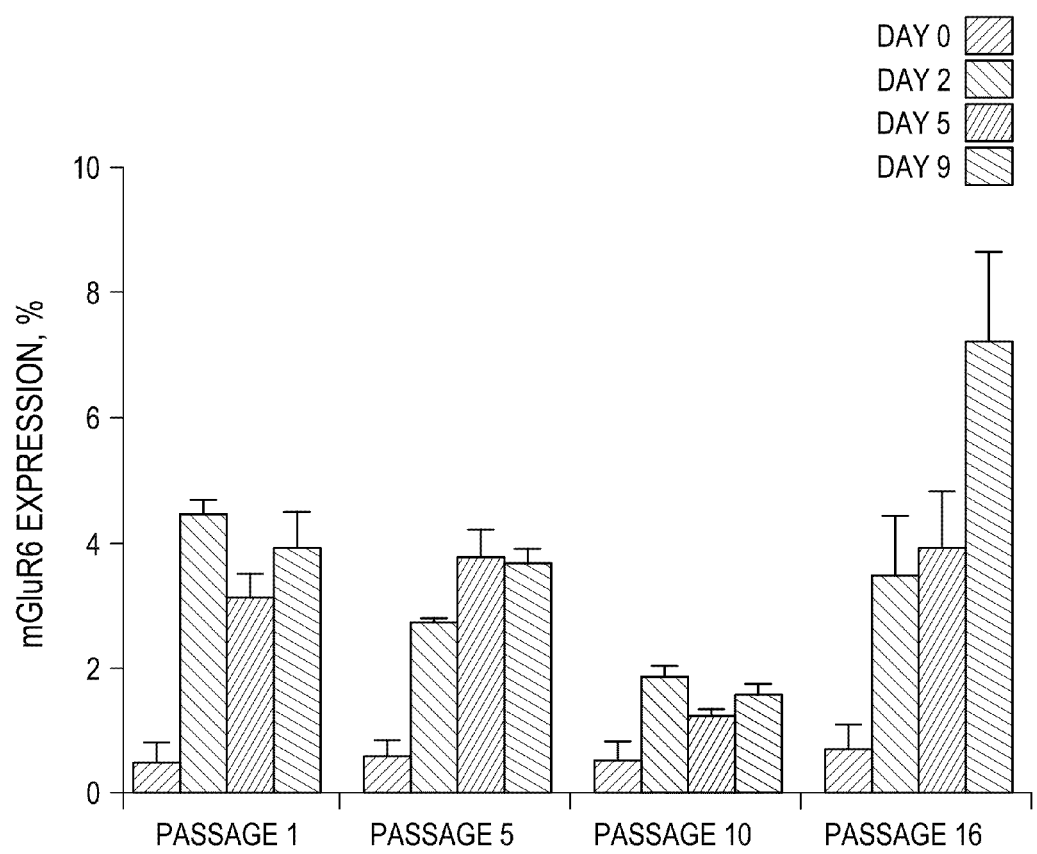
Figure 8E:
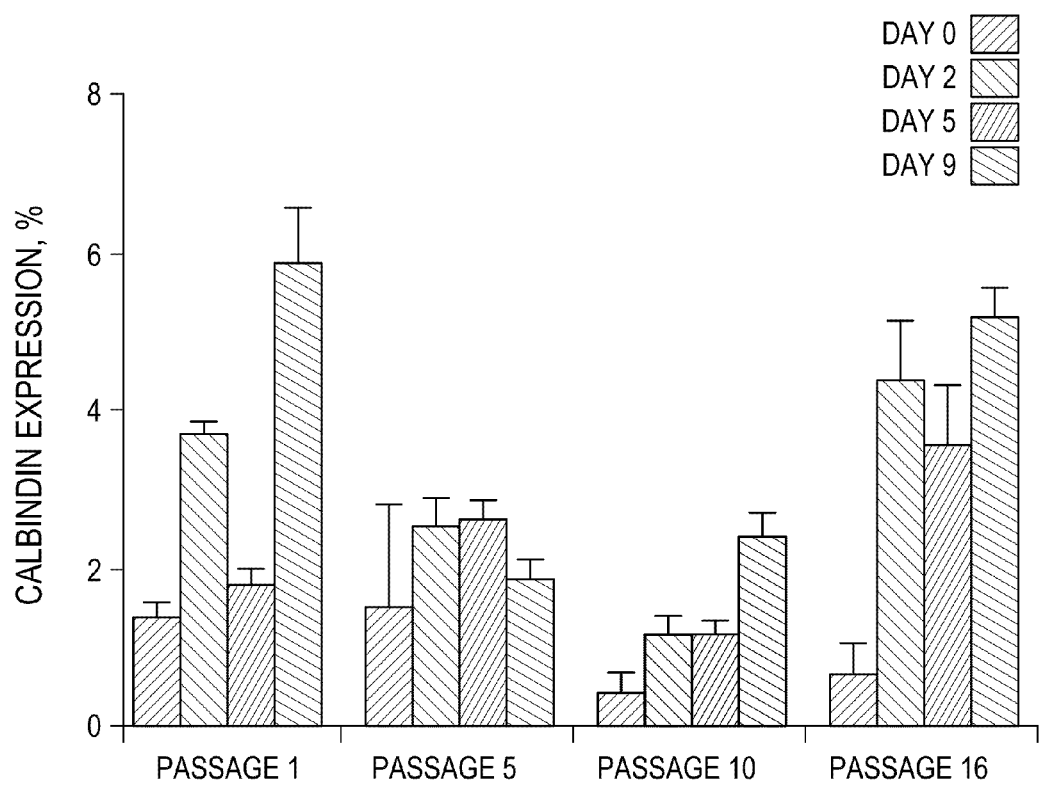
Figure 8F:
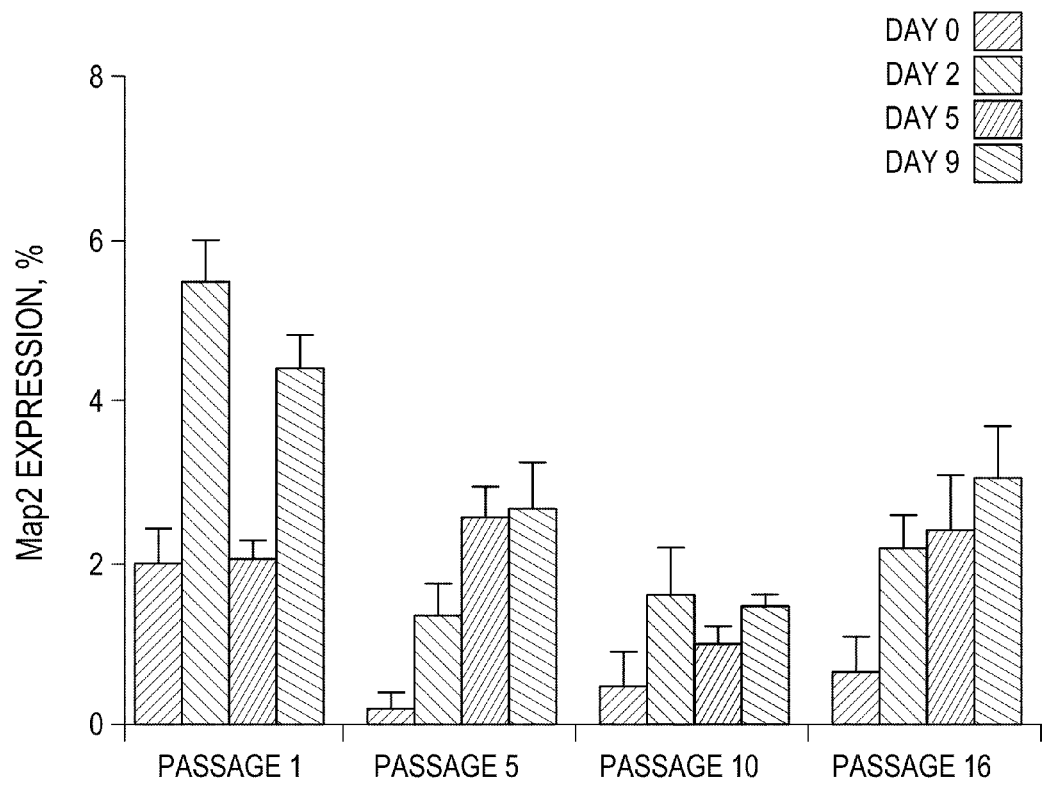

It has been shown that hRPCs express hTERT both in 3% and 20% conditions on all passages. The TRAPEZE assay has shown that telomerase activity is decreased with passage in both conditions but is higher in 3% vs. 20% oxygen conditions, and is preserved until passage 16 in low oxygen, possibly allowing retinal progenitors to divide without telomers shortening. See FIG. 6 which is a bar graph of the relative telomerase activity in hRPCs obtained for passages 1, 3, 5, 7, 10 and 16 for low and regular oxygen conditions. The telomerase products were approximately 50 bp.

Multipotency Marker

ICC and Western Blot have shown that culturing in 3% oxygen tension stabilizes HIF2 alpha, increases HIF1 alpha stabilization, and upregulates cMyc, KLF4, Oct4 and Sox2. It has also been shown that the expression of specific eye field development transcription factors (Pax6, Sox2, Otx2) and Nestin is maintained up to passage 16 in 3% oxygen conditions and up to passage 10 in 20% oxygen conditions, which suggests that they are not key factors in hRPC expansion in both conditions. Sox 2 was upregulated in 3% oxygen conditions, possible due to HIF2a activity. The same upregulation was observed for cytoplasmatic Oct4 (52 kDa, expressed perinuclearily), also due to HIF2a stabilization. Despite the fact that Pax6 and Otx2 expression was observed at all passages in maintenance conditions, the pattern changed during differentiation. Instead of equal expression (the same intensity) in all nuclei, a dominant subpopulation with upregulated Pax6 appeared. Otx2 expression shifted from whole cell (nucleus and cytoplasm) to nucleus only, but it was still expressed in most cells. Sox2 expression decreased during differentiation. SSEA4 upregulation in low oxygen conditions, shown for MIAMI and hESC cells, holds for hRPC cells only after passage 3. During isolation and on passage 1, the number of SSEA4 expressing cells was lower in 3% oxygen conditions, but increased on passage 3 and later passages.

Differentiation

The main characteristics of hRPC cells are functional—the ability to differentiate into specialized retinal cells. The ability of hRPC's (passage 3) to generate about 35% recoverin expressing cells, 7% blue-opsin expressing cells, and 15% of rhodopsin expressing cells after expansion in 20% oxygen tension and 7 days in differentiating conditions (media supplemented with 5% FBS without mitogens) was previously observed. Under the same conditions, recoverin, CRX or opsin-positive cells were not detected after differentiation of passage 6 hRPCs. During cell expansion under 3% oxygen conditions, it has been shown that culturing the cells under low oxygen tension in maintenance conditions does not drive spontaneous differentiation of human retinal progenitor cells into rods, cones, ganglion, bipolar or glial cells (less than 0.5% in maintenance conditions according to ICC staining) See FIGS. 7 and 8.

Summarizing the results of the above experiments, hRPCs expanded in 3% oxygen are able to generate specialized retinal cells (photoreceptors), including rods and cones. On passage 1 compared to other passages (5, 10, 16), higher amounts of specialized cells were observed after differentiation. hRCPs on passage 1 tended to form more specialized cells on day 2 as compared to other passages, which suggests that the cell culture on early passage is rich with "easy differentiating precursors" that are lost during expansion. The ability of hRPCs to generate specialized retinal cells is greatly decreased on other passages as compared to passage 1, but is relatively constant between later passages. This suggests that progenitors cultured in 3% oxygen under maintenance conditions do not lose the ability to generate photoreceptors, ganglion or bipolar cells. On later passages, less photoreceptors were generated, but more bipolar and glial cells. During differentiation, the downregulation of Pax6 (according to ICC staining, cells continue to express this marker, but at lower levels) and Sox2 (the staining pattern switches from nuclear to perinuclear and cytoplasmic) was observed.

The human retinal progenitor cells of the invention may be used for studying the development of the retina and eye, as well as factors affecting such development, whether beneficially or adversely. These hRPCs can also be used for clinical trials by transplantation into a suffering from dysfunctions of the eye. They may be used advantageously to repopulate or to rescue a dystrophic ocular tissue, particularly a dysfunctional retina. Retinal dysfunction encompasses any lack or loss of normal retinal function, whether due to disease, mechanical or chemical injury, or a degenerative or pathological process involving the recipient's retina. The hRPCs may be injected or otherwise placed in a retinal site, the subretinal space, vitreal cavity, or the optic nerve, according to techniques known in the art. This includes the use of biodegradable substrates as a carrier for the hRPCs.

Advantageously, the hRPCs of the invention may be used to compensate for a lack or diminution of photoreceptor cell function. Examples of retinal dysfunction that can be treated by the retinal stem cell populations and methods of the invention include but are not limited to: photoreceptor degeneration (as occurs in, e.g., retinitis pigmentosa, cone dystrophies, cone-rod and/or rod-cone dystrophies, and macular degeneration); retina detachment and retinal trauma; photic lesions caused by laser or sunlight; a macular hole; a macular edema; night blindness and color blindness; ischemic retinopathy as caused by diabetes or vascular occlusion; retinopathy due to prematurity/premature birth; infectious conditions, such as, e.g., CMV retinitis and toxoplasmosis; inflammatory conditions, such as the uveitidies; tumors, such as retinoblastoma and ocular melanoma; and for the replacement of inner retinal neurons, which are affected in ocular neuropathies including glaucoma, traumatic optic neuropathy, and radiation optic neuropathy and retinopathy.

The treatments described herein can be used as stand alone therapies, or in conjunction with other therapeutic treatments. Such treatments can include the administration of a substance that stimulates differentiation of the neuroretina-derived stem cells into photoreceptors cells or other retinal cell types (e.g., bipolar cells, ganglion cells, horizontal cells, amacrine cells, Mueller cells).

From the foregoing, it will be appreciated that, although specific embodiments of the invention have been described herein for purposes of illustration, various modifications may be made without deviating from the spirit and scope of the invention as set forth in the appended claims. All publications, patents, and patent applications referenced herein are incorporated by reference in their entirety.

What is claimed is:

1. A method of expanding multipotent human retinal progenitor cells in vitro and maintaining the multipotency of said cells in vivo, said method comprises the steps of
    establishing a cell culture comprising isolated retinal multipotent progenitor cells, and
    culturing said cells under low oxygen conditions of from about 1% to about 6% oxygen content of the culture medium and for an effective amount of time while maintaining multipotency of said cells to provide an expanded population of multipotent retinal progenitor cells,
    wherein said retinal progenitor cells express both express both HIF1 alpha and HIF2 alpha.

2. The method of claim 1 further comprising isolating the expanded population of cells from the culture media.

3. The method of claim 2 further comprising transplanting said cells into a host.

4. The method of claim 3 further comprising measuring said cells cultured under low oxygen conditions for multipotency.

5. The method of claim 1 further comprising culturing said cells in the presence of at least one exogenous growth factor.

6. The method of claim 1 wherein the effective amount of time comprises at least 10 passages in the low oxygen conditions.

7. The method of claim 1 wherein the oxygen content of the culture medium is from about 2% to about 4%.

8. The method of claim 1 where the retinal progenitor cells are obtained from post-natal retinal tissue.

9. The method of claim 1 wherein the retinal progenitor cells are obtained from the retinal neurosphere.

* * * * *